United States Patent
Dijkhuizen et al.

(10) Patent No.: US 10,808,271 B2
(45) Date of Patent: Oct. 20, 2020

(54) ALPHA GLUCANS

(71) Applicant: NESTEC S.A., Vevey (CH)

(72) Inventors: Lubbert Dijkhuizen, AG Groningen (NL); Joana Gangoiti Munecas, AG Groningen (NL); Sander Sebastiaan Van Leeuwen, AG Groningen (NL); Christina Vafeiadi, Lausanne (CH); Stephane Duboux, St-Prex (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 16/305,272

(22) PCT Filed: May 31, 2017

(86) PCT No.: PCT/EP2017/063214
§ 371 (c)(1),
(2) Date: Nov. 28, 2018

(87) PCT Pub. No.: WO2017/207663
PCT Pub. Date: Dec. 7, 2017

(65) Prior Publication Data
US 2019/0330671 A1    Oct. 31, 2019

(30) Foreign Application Priority Data
Jun. 2, 2016  (EP) .................................... 16172606

(51) Int. Cl.
| | |
|---|---|
| C12P 19/18 | (2006.01) |
| C12N 9/26 | (2006.01) |
| C12N 9/44 | (2006.01) |
| C12P 19/00 | (2006.01) |
| A23L 33/21 | (2016.01) |
| A23K 20/189 | (2016.01) |
| C12P 19/04 | (2006.01) |

(52) U.S. Cl.
CPC ............... *C12P 19/18* (2013.01); *A23L 33/21* (2016.08); *A23K 20/189* (2016.05); *C12P 19/04* (2013.01)

(58) Field of Classification Search
CPC ........ C12N 9/2428; C12P 19/04; C12P 19/02; C12P 19/14; C12Y 204/00; C12Y 302/01039
USPC ......... 435/101, 102, 193, 201, 152.2, 252.5, 435/205
See application file for complete search history.

(56) References Cited

FOREIGN PATENT DOCUMENTS

EP    2248907    11/2010

OTHER PUBLICATIONS

Davos et al., Proteins: Structure, Function and Genetics, 2000, vol. 41: 98-107.*
Wristlock et al., Quarterly Reviews of Biophysics 2003, vol. 36 (3): 307-340.*
Kwiatkowski et al., Biochemistry 38:11643-11650, 1999.*
Kisselev L., Structure, 2002, vol. 10: 8-9.*
Meng et al. "Structure-function relationships of family GH70 glucansucrase and 4,6-alpha-glucanotransferase enzymes, and their evolutionary relationships with family GH13 enzymes" Cellular and Molecular Life Sciences, 2016, vol. 73, pp. 2681-2706.
Vuillemin et al. "Characterization of the first alpha-(1-3) branching sucrases of GH70 family" Journal of Biological Chemistry Jan. 13, 2016, vol. 291, No. 14, pp. 7687-7702, XP055320418.
Kralj et al. "Glucan synthesis in the genus *Lactobacillus*: isolation and characterization of glucansucrase genes, enzymes and glucan products from six different strains" Microbiology, 2004, vol. 150, pp. 3681-3690.
Barretto et al. "Genome Sequence of *Lactobacillus fermentum* Strain NCC2970" Genome Announcements, Nov./Dec. 2016, vol. 4, issue 6, e01254-16.
Meng et al. "Synthesis of New Hyperbranched alpha-Glucans from Sucrose by *Lactobacillus reuteri* 180 Glucansucrase Mutants" Journal of Agricultural and Food Chemistry, 2016, vol. 64, pp. 433-442.
Leemhuis et al. "Glucansucrases: Three-dimensional structures, reactions, mechanism, alpha-glucan analysis and their implications in biotechnology and food applications" Journal of Biotechnology, 2013, vol. 163, pp. 250-272.
Irague et al. "Structure and Property Engineering of alpha-D-Glucans Synthesized by Dextransucrase Mutants" Biomacromolecules, 2012, vol. 13, pp. 187-195.
Woranovicz-Barreira et al. "Chemotyping glucans from lichens of the genus *Cladonia*" Phytochemistry, 1999, vol. 52, pp. 1069-1074.
Carbonero et al. "Polysaccharides of lichenized fungi of three *Cladina* spp.: significance as chemotypes" Phytochemistry, 2002, vol. 61, pp. 681-686.

\* cited by examiner

*Primary Examiner* — Robert B Mondesi
*Assistant Examiner* — Mohammad Y Meah
(74) *Attorney, Agent, or Firm* — K&L Gates LLP

(57) ABSTRACT

The present invention relates to the field of poly- and oligosaccharides and their dietary effects. In particular it relates to a method of producing an α-glucan containing (α1→3) linked D-glucose units. The invention also provides a branched α-glucan comprising alternating (α1→4) and (α1→3) glucosidic linkages and having (α1→3,4) branching points, a food composition, and the use of an α-glucanotransferase enzyme for reducing the digestible carbohydrates of a starch containing food material. Further aspects of the invention are a bacteria, an enzyme and an expression vector.

11 Claims, 10 Drawing Sheets
Specification includes a Sequence Listing.

Figure 2

| Bacterial strain | NCBI accession numbers | Specificity | Motif II | Motif III | Motif IV | Motif I |
|---|---|---|---|---|---|---|
| | | | 3  4 | 5 | 67 | 1  2 |
| A | | | | | | |
| L. fermentum NCC 2970 | | 4,3-α-GT | 983 GFRIDAADDMD | 1020 HLSYNEGYGPG | 1092 YVTNHDIR--ANLINQ | 1446 EDIVMNQ |
| B | | | | | | |
| Lactobacillus reuteri 121 (GtfB) | AAU08014.2 | 4,6-α-GT | 1011 GFRVDAADNID | 1048 HLSYNEGYHSG | 1120 FVTNHDQR--KNLINR | 1478 EDIVMNQ |
| Lactobacillus reuteri ML1 (ML4) | AAU08003.2 | 4,6-α-GT | 1012 GFRVDAADNID | 1049 HLSINEGYHSG | 1121 FVTNHDQR--KNLINR | 1479 EDLVMNQ |
| Lactobacillus reuteri DSM 20016 (GtfW) | ABC83597.1 | 4,6-α-GT | 748 GFRVDAADNID | 785 HLVVNEGYHSG | 858 FVTNHDQR--KNVINQ | 1215 EDLVMNQ |
| Lactobacillus salivarius GJ-24 | EGM52218.1 | ND | 1026 GFRIDAADHID | 1063 HLSYNEGYRSG | 1134 YVTNHDQR--ANLINQ | 1485 VDIVMNQ |
| Pediococcus pentosaceus IE-3 | CCG90643.1 | ND | 380 GFRVDAADNID | 417 HLSYNEGYHSG | 489 FVTNHDQR--KNLINS | 841 EDIVMNQ |
| Lactobacillus plantarum 16 | WP_016526729.1 | ND | 749 GFRVDAADHID | 786 HLVINEGYNYG | 859 FVTNHDQR--NNLVNR | 1201 EDLVMNQ |
| Lactobacillus fermentum ATCC 14931 | EEI21226.1 | ND | 406 GFRIDAADNID | 443 HLIINEGYHSG | 512 FVTNHDQR--KNLINQ | 862 EDLVMNQ |
| Lactobacillus acidipiscis KCTC 13900 | WP_035631372.1 | ND | 296 GFNDAADNID | 333 HLVVNEGYHSG | 406 FVTNHDQR--KNVINQ | 765 VIMVMNQ |
| Lactobacillus delbrueckii JCM 17838 | WP_050952694.1 | ND | 265 GFRIDAADNID | 302 HLSYNEGYHLG | 374 FVTNHDQR--KNLINR | 732 EDIVMNQ |
| Lactobacillus panis DSM 6035 | KRM25865.1 | ND | 988 GFRVDAADNVD | 1025 HLIVNEGYHSD | 1097 FVTNHDQR--ANLINQ | 1455 EDLVMNQ |
| Leuconostoc mesenteroides | WP_059442690.1 | ND | 252 GFRIDAADHID | 289 HLIYNEGYRSG | 360 FVTNHDQR--ANLING | 711 EDIVMNQ |
| C | | | | | | |
| Exiguobacterium sibiricum 255-15 | ACB62096.1 | | 403 GFRIDAASHYD | 433 HLSIYESYKSE | 504 FVNNHDQR--KNRVNQ | 138 MDLVPNQ |
| D | | | | | | |
| Azotobacter chroococcum NCIMB 8003 | AJE22990.1 | 4,6-α-GT | 467 GFRIDAASHIN | 500 HLSYESYVTQ | 567 FVNNHDQR--HNIIVT | 202 VDVVPNQ |
| | | | NU | A/B | TS | |
| E | | | | | | |
| Lactobacillus reuteri 180 (Gtf180) | AAU08001.1 | Dextransucrase | 1021 GIRVDAVDNVD | 1058 HINILEDWGRD | 1131 FVRAHDSWAQDQIRQ | 1503 ADWVPDQ |
| Lactobacillus reuteri 121 (GtfA) | AAU08015.1 | Reuteransucrase | 1020 SVRVDAPDNID | 1056 HINILEDWNHA | 1128 FVRAHDNSQDQIQN | 1508 ADWVPDQ |
| Streptococcus mutans SI (GtfSI) | BAA26114.1 | Mutansucrase | 473 SIRVDAVDNVD | 510 HLSILEAWSYN | 583 FIRAHDSEVQDLIRD | 954 ADWVPDQ |
| Leuconostoc mesenteroides NRRL-1355 | CAB65910.2 | Alternansucrase | 631 GIRVDAVDNVD | 668 HLSILEDWNGK | 762 FVRAHDYDAQDPIRK | 1168 ADWVPDQ |
| Leuconostoc citreum NRRL B-1299 | CDX66820.1 | (1→2) Branching sucrase | 2206 SIRLDAVDFIH | 2243 HLSILVEAGLDA | 2317 IIHARDKGVQERVGA | 2688 ADVVDNQ |
| Leuconostoc citreum NRRL B-742 | CDX65123.1 | (1→3) Branching sucrase | 667 SMRLDAISFVD | 704 HISIVEAPKGE | 783 IVHAHDIODTVIH | 1182 ADFVANQ | a. H5 of →4)-α-D-Glcp-(1→3)-
b. H3 of →4)-α-D-Glcp-(1→3)-
c. H3 of →4)-α-D-Glcp-(1→4)-
d. H4 of α-D-Glcp-(1→3)-
e. H4 of α-D-Glcp-(1→4)-
f. H4:C4 of →4)-α-D-Glcp-
g. H3:C3 of →3)-α-D-Glcp-
y. interresidual H1:H3
z. interresidual H1:H4

ALPHA GLUCANS

CROSS REFERENCE TO RELATED APPLICATIONS

The present application is a National Stage of International Application No. PCT/EP2017/063214, filed on May 31, 2017, which claims priority to European Patent Application No. 16172606.2, filed on Jun. 2, 2016, the entire contents of which are being incorporated herein by reference.

FIELD OF THE INVENTION

The present invention relates to the field of poly- and oligosaccharides and their dietary effects. In particular it relates to a method of producing an α-glucan containing (α1→3) linked D-glucose units. The invention also provides a branched α-glucan comprising alternating (α1→4) and (α1→3) glucosidic linkages and having (α1→3,4) branching points, a food composition, and the use of an α-glucanotransferase enzyme for reducing the digestible carbohydrates of a starch containing food material. Further aspects of the invention are a bacteria, an enzyme and an expression vector.

BACKGROUND OF THE INVENTION

The prevalence of obesity and being overweight is rapidly increasing worldwide. The development of foods with high satiating capacities and low energy densities may help to prevent weight gain and to stimulate weight loss. Consumption of food and drinks containing non-digestible carbohydrates instead of sugars induces a lower blood glucose rise after meals compared to sugar-containing food and drinks.

The most common carbohydrate in human diets is starch. This polysaccharide is produced by most green plants as an energy store. It is contained in large amounts in such staple foods as potatoes, wheat, maize, rice, and cassava. Various methods have been proposed for the chemical modification of starch and malto-oligosaccharides into non-digestible carbohydrates.

EP2427565 describes the use of a glucanotransferase enzyme of *Lactobacillus reuteri* 121 GTFB to convert starch into linear gluco-oligosaccharides containing relatively long isomalto-oligosaccharide units. Such materials are partially resistant to digestion and hence give less glucose production on consumption, contributing to the prevention of obesity and type II diabetes.

Amylose is an α-glucan having exclusively (α1→4) linkages and high digestibility. Introducing (α1→3) linked D-glucose units reduces the digestibility. Lichens from the genus *Cladonia* produce α-glucans with alternate (α1→3) and (α1→4) linkages in linear structures [Woranovicz-Barreira et al., Phytochemistry, 52, 1069-1074 (1999)], but these α-glucans are water insoluble, limiting their dietary applications.

It would be desirable to provide further means for the enzymatic modification of starch, starch derivatives and malto-oligosaccharides in order to change their functional properties and enhance their nutritional value. The materials obtained should ideally combine low digestibility with good solubility. In particular it would be beneficial to provide enzymes to perform such modifications which are suitable for use in food manufacture and exhibit good enzyme activity and thermostability.

Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

An object of the present invention is to improve the state of the art and to provide an improved solution for the enzymatic modification of starch and other polysaccharide or oligosaccharide into materials having reduced digestibility, or at least to provide a useful alternative. The object of the present invention is achieved by the subject matter of the independent claims. The dependent claims further develop the idea of the present invention.

Accordingly, the present invention provides in a first aspect a method of producing an α-glucan containing (α1→3) linked D-glucose units, the method comprising contacting a polysaccharide or oligosaccharide substrate comprising at its non-reducing end at least two (α1→4) linked D-glucose units with an α-glucanotransferase enzyme capable of cleaving (α1→4) glucosidic linkages and introducing new (α1→3) glucosidic linkages to form a glucose polymer having linear segments of (α1→4) linked D-glucose units interspersed with (α1→3) glucosidic linkages, without forming consecutive (α1→3) glucosidic linkages; wherein said α-glucanotransferase is selected from the group consisting of GTFB, GTFC and GTFD types of enzyme, or a functional homolog thereof having the specified enzymatic activity.

In a second aspect, the invention relates to an α-glucan comprising linear segments of (α1→4) linked D-glucose units interspersed with (α1→3) glucosidic linkages and having (α1→3,4) branching points wherein the α-glucan has a ratio of branching of at least 3%, comprises less than 1 wt. % consecutive (α1→3) linkages and has an average molecular mass between $5 \times 10^2$ Da and $1 \times 10^7$ Da. A third aspect of the invention relates to a food composition comprising an α-glucan comprising linear segments of (α1→4) linked D-glucose units interspersed with (α1→3) glucosidic linkages and having (α1→3,4) branching points wherein the α-glucan has a ratio of branching of at least 3%, comprises less than 1 wt. % consecutive (α1→3) linkages and has an average molecular mass between $5 \times 10^2$ Da and $1 \times 10^7$ Da.

A further aspect of the invention is the use of an α-glucanotransferase enzyme that comprises an amino acid sequence having at least 80% identity to SEQ ID NO:1 for reducing the digestible carbohydrates of a starch containing food material. A still further aspect of the invention is the bacterial strain *Lactobacillus fermentum* CNCM I-5068 (NCC 2970).

Lactic acid bacteria possess a diversity of glucansucrase (GS) enzymes that belong to glycoside hydrolase family 70 (GH70) and convert sucrose into α-glucan polysaccharides via the formation of (α1→2)-, (α1→3)-, (α1→4)- and/or (α1→6)-glycosidic bonds. In recent years 3 novel subfamilies of GH70 enzymes, inactive on sucrose but using maltodextrins/starch as substrates, have been established (e.g. GTFB of *Lactobacillus reuteri* 121, described in EP2248907). Compared to the broad linkage specificity found with GSs, all characterized non-sucrose utilizing GH70 enzymes exclusively display 4,6-α-glucanotransferase activity (4,6-α-GTase). They cleave (α1→4)-linkages and synthesize new (α1→6)-linkages, yielding a linear (α1→6) α-glucan chain or a branched polymer with alternating α(1→4)/(1→6) linkages.

The inventors identified a single gene coding for a putative GTFB-like enzyme (1593 amino acids, 180 kDa) in the genome of *Lactobacillus fermentum* NCC 2970. This protein shares 77% sequence identity with the *L. reuteri* 121 GTFB 4,6-α-GTase, but shows unique variations in some of the residues forming the substrate binding residues in GSs. Biochemical characterization of this *L. fermentum* GTFB enzyme, including a detailed structural analysis of its products from amylose, revealed that it acts as a 4,3-α-glucanotransferase (4,3-α-GTase) cleaving (α1→4)-linkages and forming new (α1→3)-linkages in linear or branched orientation. This enzyme is unable to synthesize consecutive (α1→3)-linkages and its activity results in the formation of a novel type of α-glucan with alternating α(1→3)/(1→4)-linkages and with (1→3,4) branching points. The discovery of this novel reaction specificity in GH70 family and clan GH-H expands the range of α-glucans that can be synthesized and allows the identification of key positions governing the linkage specificity within the active site of the GTFB-like GH70 subfamily of enzymes.

1D $^1$H NMR analysis of the α-glucan formed by the *Lactobacillus fermentum* GTFB enzyme revealed the presence of (α1→4) and (α1→3) linkages. Methylation analysis of the α-glucan revealed the presence of terminal, 3-substituted, 4-substituted, and 3,4-disubstituted glucopyranose residues. The presence of 3-substituted, and 3,4-disubstituted glucopyranose residues means that the GTFB enzyme forms (α1→3) linkages in linear and branched orientation. Only trace amounts (less than 1%) of (α1→6) linkages were detected. No evidence was observed for two consecutive (α1→3)-linked glucopyranose residues by 2D NMR spectroscopy and Smith degradation analysis. Thus, all 3-substituted glucopyranose residues detected by methylation analysis must either be (α1→4) linked, forming a (α1→3) branching point in the structure, or be part of a linear segment of (α1→4) linkages interspersed with single (α1→3) linkages.

DESCRIPTION OF THE DRAWINGS

FIG. 2 shows the sequence alignment of conserved motifs I-IV in the catalytic domain of the *L. fermentum* 4,3-α-GT GTFB enzyme (A), (putative) GTFB-like 4,6-α-GTase enzymes (B), *E. sibiricum* GTFC 4,6-α-GTase enzyme (C), *A. chroococcum* GTFD 4,6-α-GTase enzyme (D), and glucansucrase enzymes (E). The seven strictly conserved amino acid residues in GH70 enzymes (indicated by the numbers 1 to 7 above the sequences) are also conserved in the novel *L. fermentum* 4,3-α-GT GTFB protein. Amino acids that constitute the catalytic triad are shown in bold and lightly shaded. Symbols: NU=nucleophile, A/B=general acid/base, TS=transition state stabilizer. Figure discloses SEQ ID NOs: 5-84, respectively, in order of appearance.

(w v$^{-1}$) amylose V with the *L. fermentum* GTFB enzyme (25 µg ml$^{-1}$ recorded at 300K in D2O. Peaks for (α1→4) and (α1→3) anomeric signals have been indicated. Structural-reporter signals are indicated.

Figure 10:
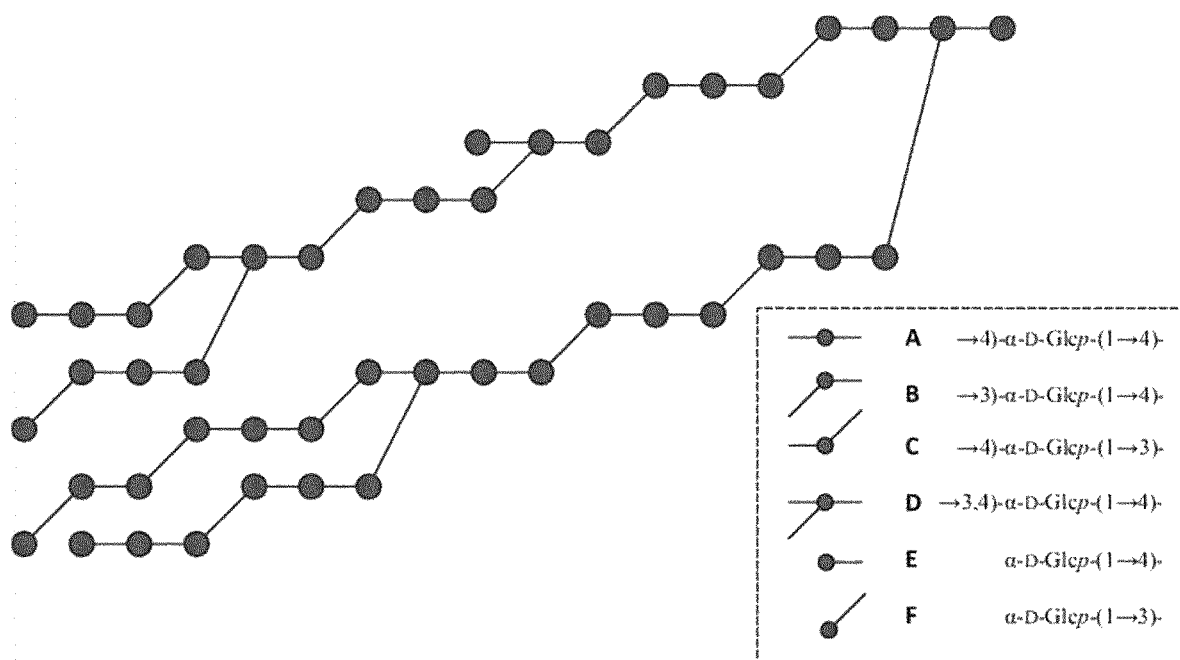

FIG. 10 is a composite model of the *L. fermentum* GTFB polysaccharide product, taking into account all structural elements identified by 1D and 2D NMR spectroscopy analysis, methylation analysis and Smith Degradation analysis. Residue labels correspond with those in Table 3.

Figure 11:
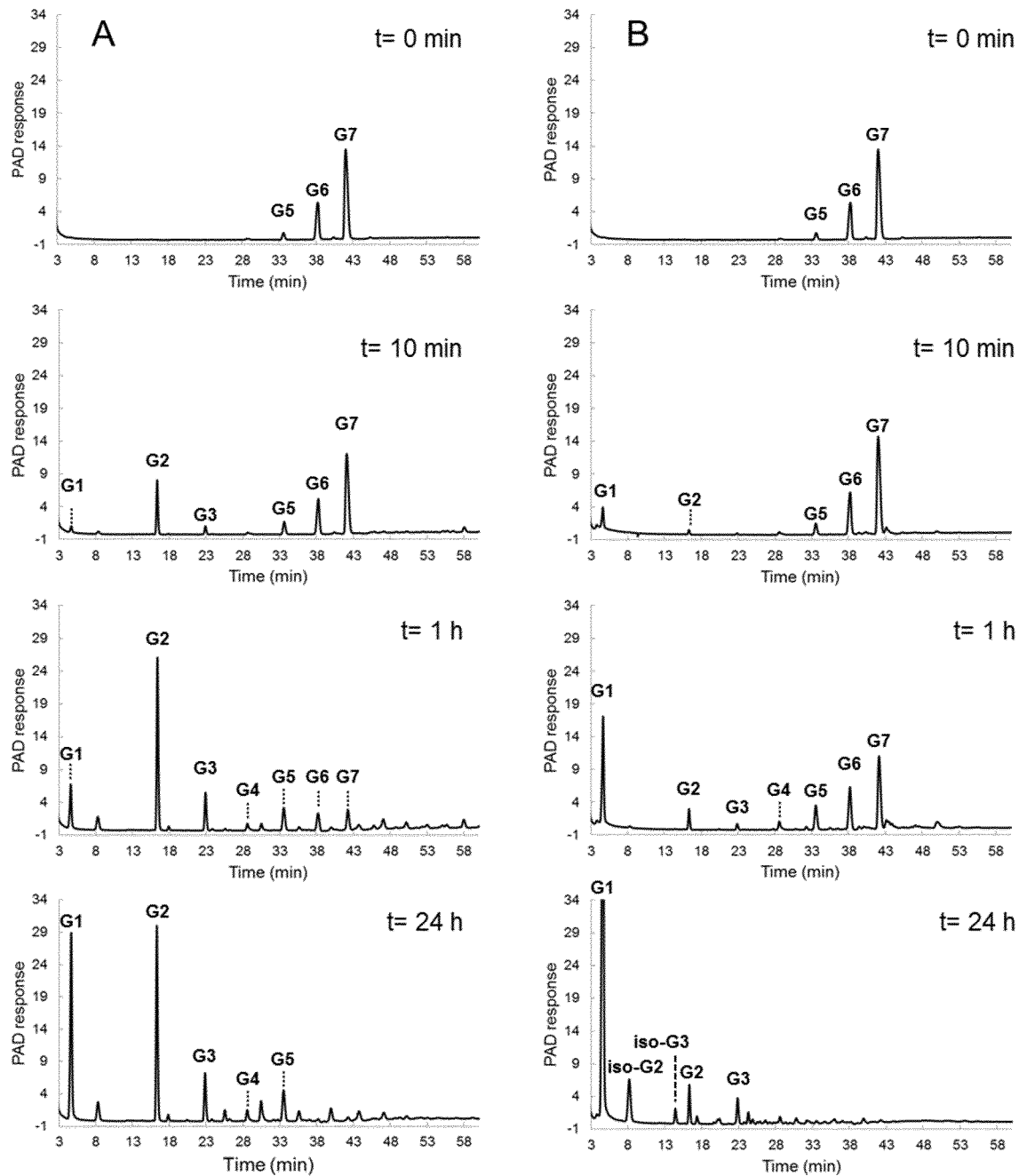

FIG. 11 shows a HPAEC-PAD profile of the oligosaccharide mixture formed upon the incubation of maltoheptaose with 25 µg ml$^{-1}$ of (A) *L. fermentum* GTFB, and (B) *L. reuteri* 121 GTFB for t=10 min, 1 h, and 24 h (pH 5.5, 37° C.). Established oligosaccharide structures. The identity of peaks was assigned using commercial oligosaccharide standards.

Figure 12:
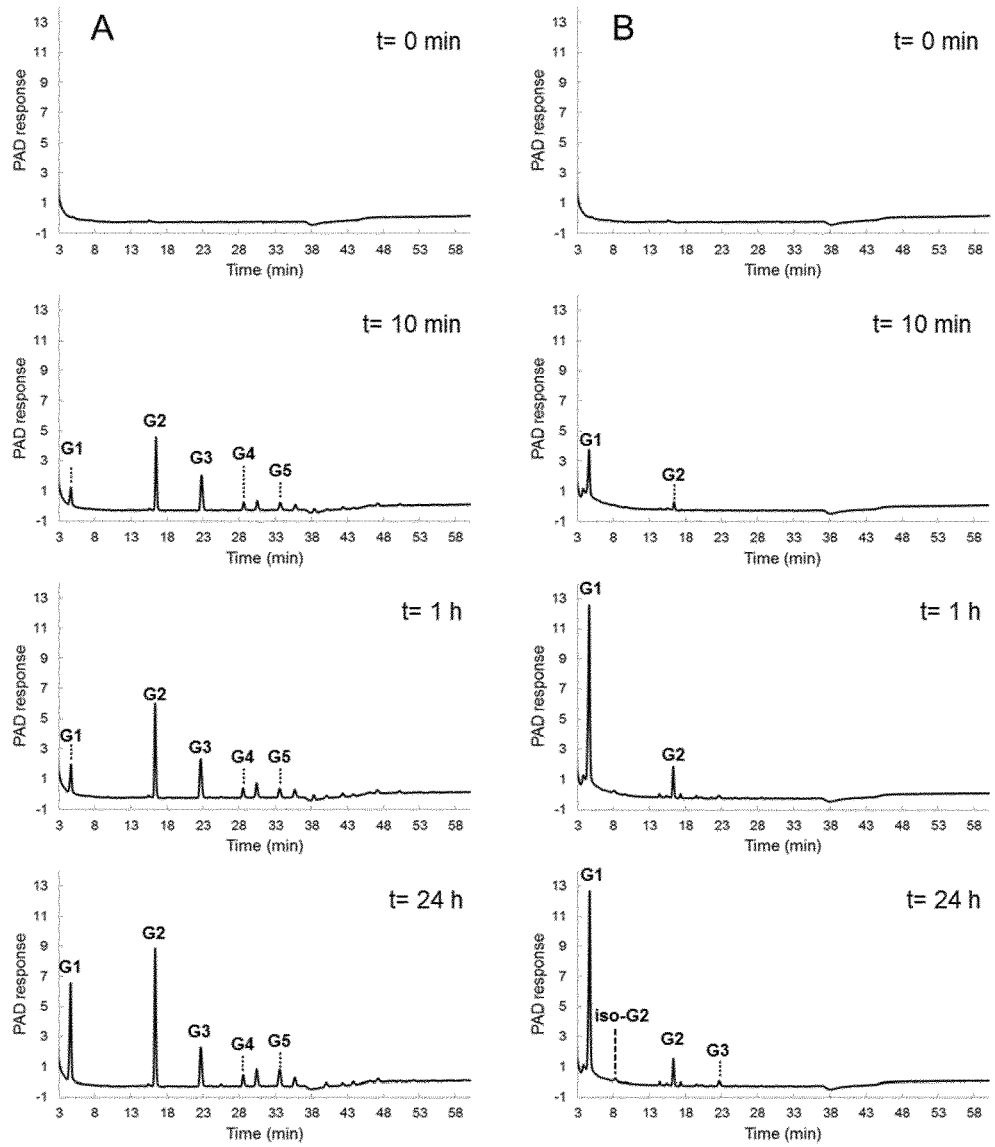

FIG. 12 shows a HPAEC-PAD profile of the oligosaccharide mixture formed upon the incubation of amylose V with 25 µg ml$^{-1}$ of (A) *L. fermentum* GTFB, and (B) *L. reuteri* 121 GTFB for t=10 min, 1 h, and 24 h (pH 5.5, 37° C.). Established oligosaccharide structures. The identity of peaks was assigned using commercial oligosaccharide standards.

Figure 13:
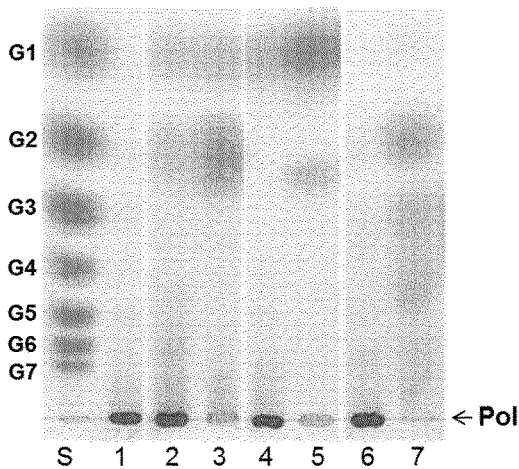

FIG. 13 is a TLC analysis of the *L. fermentum* GTFB polymer after treatment with *Aspergillus oryzae* α-amylase, *Chaetomium erraticum* dextranase and *Klebsiella planticola* pullulanase M1. Lane 1, *L. fermentum* GTFB polymer before the enzymatic treatments; Lanes 2-3, product mixtures generated by the α-amylase enzymatic treatment of the *L. fermentum* GTFB polymer and starch, respectively. Lanes 4-5, product mixtures generated by the dextranase enzymatic treatment of the *L. fermentum* GTFB polymer and IMMP, respectively. Lanes 6-7, product mixtures generated by the pullulanase enzymatic treatment of the *L. fermentum* GTFB polymer and the *A. chroococcum* GTFD polymer, respectively. Lane S, standard; G1, glucose; G2-G7, maltose to maltoheptaose; Pol, polymer.

DETAILED DESCRIPTION OF THE INVENTION

Consequently the present invention relates in part to a method of producing an α-glucan containing (α1→3) linked D-glucose units, the method comprising contacting a polysaccharide or oligosaccharide substrate comprising at its non-reducing end at least two (α1→4) linked D-glucose units with an α-glucanotransferase enzyme capable of cleaving (α1→4) glucosidic linkages and making new (α1→3) glucosidic linkages to form a glucose polymer having linear segments of (α1→4) linked D-glucose units interspersed with (α1→3) glucosidic linkages, without forming consecutive (α1→3) glucosidic linkages; wherein said α-glucanotransferase is selected from the group consisting of GTFB, GTFC and GTFD types of enzyme (for example a GTFB type of enzyme), or a functional homolog thereof having the specified enzymatic activity.

Polysaccharides are polymeric carbohydrate molecules composed of long chains of monosaccharide units bound together by glycosidic linkages. Oligosaccharides are saccharide polymers containing a small number (typically three to nine) of monosaccharides. Glucose polymers are saccharide polymers where the monosaccharide is glucose. α-Glucans are polysaccharides of D-glucose monomers linked with glycosidic bonds of the alpha form. An example of a substrate comprising at its non-reducing end at least two (α1→4) linked D-glucose units is amylose.

Linear segments are parts of the polymer's structure which are not branched, for example a chain of mono-substituted glucopyranose residues. In the context of the present invention, the term "interspersed" means occurring between. In the linear segments of (α1→4) linked D-glucose units interspersed with (α1→3) glucosidic linkages, the sequence of linkages has one or more (α1→4) linkages, then an (α1→3) linkage and then one or more (α1→4) linkages. In the linear segment the (α1→3) linkage occurs between (α1→4) linkages. The (α1→3) glucosidic linkages in this configuration are sometimes called "bridging" linkages.

The method of the invention may comprise contacting a polysaccharide or oligosaccharide substrate comprising at its non-reducing end at least two (α1→4) linked D-glucose units with an α-glucanotransferase enzyme capable of cleaving (α1→4) glucosidic linkages and making new (α1→3) glucosidic linkages to form a glucose polymer having linear segments of (α1→4) linked D-glucose units interspersed with (α1→3) glucosidic linkages, without forming consecutive (α1→3) glucosidic linkages; wherein said α-glucanotransferase is capable of forming (α1→3,4) branching points and is selected from the group consisting of GTFB, GTFC and GTFD types of enzyme (for example a GTFB type of enzyme), or a functional homolog thereof having the specified enzymatic activity.

The α-glucan produced by the method of the invention may have a ratio of branching of at least 3%, for example at least 5%, for further example at least 7%. In the context of the present invention, the ratio of branching is defined as the total number of branching anhydroglucose units (AGU), i.e. AGU being bound to three other units, with respect to the total number of AGU of a molecule. The ratio of branching can be determined by methods known in the art, such as methylation followed by gas chromatography. The more branching is present in an α-glucan, the less access is provided to digestive enzymes and so the α-glucan can present a lower digestibility. In addition, the presence of branching points can increase the solubility of the α-glucan. It is advantageous that the method of the invention can provide an α-glucan that combines low digestibility with good solubility.

The α-glucan produced by the method of the invention may comprise at least one (α1→4) glucosidic linkage adjacent to an (α1→3) glucosidic linkage and at least one (α1→3,4) branching point. The α-glucan produced by the method of the invention may comprise between 50 and 70 percent (α1→4) glucosidic linkages, between 8 and 30 percent single (α1→3) glucosidic linkages and between 3 and 20 percent (α1→3,4) branching points, for example between 5 and 15 percent (α1→3,4) branching points. The α-glucan produced by the method of the invention may have less than 1% consecutive (α1→3) glucosidic linkages, for example it may have less than 0.5% consecutive (α1→3) glucosidic linkages, for further example it may have no consecutive (α1→3) glucosidic linkages. The α-glucan produced by the method of the invention may have less than 1% (α1→6) glucosidic linkages, for example it may have less than 0.5% (α1→6) glucosidic linkages, for further example it may have no (α1→6) glucosidic linkages. The percentage of linkages refers to the number of linkages as a percentage of the total number of linkages.

Four conserved regions have been identified in the catalytic domain of GTF enzymes. Previous protein engineering studies have demonstrated that amino acid residues located in conserved sequence region III and IV (see FIG. 2 for a sequence alignment) control the product specificity of GTF enzymes regarding the glycosidic bond type formed. Also region I and region II contain amino acid residues that contribute to enzyme activity and reaction specificity. The α-glucanotransferase in the method of the invention may comprise at least one of the following mutations within the conserved regions of the GTFB protein (see FIG. 2).

A) (conserved region II): An Asp at D991 (instead of a Asn at N1019 in *L. reuteri* GTFB 4,6-α-glucanotransferase)

B) (conserved region IV): An Ile at 11098 (instead of a Gln at Q1126 in *L. reuteri* GTFB 4,6-α-glucanotransferase)

C) (conserved region IV): An Asn at N1100 (instead of a Lys at K1128 in *L. reuteri* GTFB 4,6-α-glucanotransferase)

The α-glucanotransferase in the method of the invention may comprise an amino acid sequence having at least 90% identity to SEQ ID NO:1 (for example at least 92, 95, 96, 97, 98, or 99% identity to SEQ ID NO:1).

The α-glucanotransferase in the method of the invention may be a *Lactobacillus fermentum* GTFB enzyme, for example the α-glucanotransferase in the method of the invention may be a *Lactobacillus fermentum* CNCM I-5068 GTFB enzyme. In one aspect, the invention provides a method for producing an α-glucan containing (α1→3) linked D-glucose units, the method comprising contacting a polysaccharide or oligosaccharide substrate comprising at its non-reducing end at least two (α1→4) linked D-glucose units with an α-glucanotransferase comprising (for example consisting of) an amino acid sequence having at least 90% identity to SEQ ID NO:1 (for example a *Lactobacillus fermentum* CNCM I-5068 GTFB enzyme).

The substrate in the method of the invention may have a degree of polymerization of at least five, for example it may comprise at least five D-glucose units. The degree of polymerization is the number of monomeric units in a polymer or oligomer molecule. For example, the substrate in the method of the invention may have a degree of polymerization of at least six, for example it may comprise at least six D-glucose units. The substrate in the method of the invention may be selected from the group consisting of starch (for example waxy starch or high amylose starch), starch derivatives, malto-oligosaccharides, gluco-oligosaccharides, amylose, amylopectin, maltodextrins, (α1→4) glucans and combinations thereof. Starch derivatives are prepared by physically, enzymatically, or chemically treating native starch to change its properties.

The substrate in the method of the invention may be comprised within another material, for example the substrate may be starch provided in the form of flour. It is advantageous to be able to convert polysaccharides or oligosaccharides comprised within food ingredients into α-glucans with lower digestibility, for example branched α-glucans. Such a conversion may increase the fibre content of the ingredients and/or may aid in reducing the calorie content of the ingredients. The method of the invention may be performed as part of a food processing operation, for example the α-glucanotransferase enzyme may be applied to food ingredients during a process to produce a food product. The substrate may be comprised within a material which already has a positive nutritional profile, for example the substrate may be comprised within wholegrain flour.

The extent to which the polysaccharide or oligosaccharide substrate may be converted by the α-glucanotransferase enzyme in the method of the invention can be adjusted by limiting the time of reaction. Partially converted substrates will provide different physical properties. The production of α-glucan in the method of the invention may be stopped before the reaction between the substrate and the α-glucanotransferase enzyme has reached completion, for example it may be stopped by denaturing (e.g. by heat) or removing the enzyme.

The α-glucanotransferase enzyme in the method of the invention may be immobilized, for example immobilized before contacting the polysaccharide or oligosaccharide substrate. Such immobilization techniques are well known in the art. Removal of the enzyme (discussed above) may be facilitated by immobilization of the enzyme. Immobilization techniques may be selected from the group consisting of covalent binding, entrapment, physical adsorption, cross-linking and combinations of these. In immobilization by covalent binding, enzymes are covalently linked to a support through the functional groups in the enzymes that are not essential for the catalytic activity. Oxides materials such as alumina, silica, and silicated alumina can be used for covalent binding of the enzyme. In immobilization by entrapment the enzyme is localized within the lattice of a polymer matrix or membrane. Entrapment methods are classified into five major types: lattice, microcapsule, liposome, membrane, and reverse micelle. The enzyme is entrapped in the matrix of various synthetic or natural polymers. Alginate, a naturally occurring polysaccharide that forms gels by ionotropic gelation is one such immobilization matrix. Immobilization by physical adsorption is the simplest and the oldest method of immobilizing enzymes onto carriers. Immobilization by adsorption is based on the physical interactions between the enzymes and the carrier, such as hydrogen bonding, hydrophobic interactions, van der Waals force, and their combinations. Adsorption is generally less disruptive to the enzymes than chemical means of attachment. Immobilization by cross-linking utilizes bi- or multifunctional compounds, which serve as the reagent for intermolecular cross-linking of the enzymes. Cross-linking may be used in combination with other immobilization methods such as adsorption or entrapment.

The polysaccharide or oligosaccharide substrate may be contacted with an α-glucanotransferase enzyme at a temperature of between 20° C. and 60° C. (for example between 40° C. and 55° C.) and a pH of between 3.5 to 8.0 (for example between 5.5 and 7.5).

In a further embodiment the present invention pertains to an α-glucan comprising linear segments of (α1→4) linked D-glucose units interspersed with (α1→3) glucosidic linkages and having (α1→3,4) branching points wherein the α-glucan has a ratio of branching of at least 3% (for example at least 5%, for further example at least 7%), comprises less than 1% consecutive (α1→3) linkages (for example no consecutive (α1→3) linkages) and has an average molecular mass between $5\times10^2$ Da and $1\times10^2$ Da (for example between $1\times10^4$ Da and $1\times10^6$ Da). The α-glucan of the invention may have less than 50% (α1→3) linkages.

The α-glucan of the invention may have less than 1% (α1→,6) branching points, for example it may have less than 0.5% (α1→,6) branching points, for further example it may have no (α1→,6) branching points. The α-glucan of the invention may have no branches at O2, O4 or O6 positions. The α-glucan of the invention may have less than 1% (α1→6) glucosidic linkages, for example it may have less than 0.5% (α1→6) glucosidic linkages, for further example it may have no (α1→6) glucosidic linkages.

The α-glucan of the invention may comprise at least one (α1→4) glucosidic linkage adjacent to an (α1→3) glucosidic linkage and at least one (α1→3,4) branching point. The α-glucan of the invention may comprise between 50 and 70 percent (α1→4) glucosidic linkages, between 8 and 30 percent single (α1→3) glucosidic linkages and between 3 and 20 percent (α1→3,4) branching points, for example between 5 and 15 percent (α1→3,4) branching points. The α-glucan of the invention may have less than 1% consecutive (α1→3) glucosidic linkages, for example it may have less than 0.5% consecutive (α1→3) glucosidic linkages, for further example it may have no consecutive (α1→3) glucosidic linkages. The α-glucan of the invention may have less than 1% (α1→6) glucosidic linkages, for example it may have less than 0.5% (α1→6) glucosidic linkages, for further example it may have no (α1→6) glucosidic linkages.

The α-glucan of the invention can be regarded as a dietary fiber. Due to its highly branched structure, the α-glucan will resist enzymatic degradation in the upper gastrointestinal tract and end up in the large intestine where it can be fully fermented by the colonic microflora. In addition, such dietary fibres enhance satiety in humans or animals. Blood sugar levels rise after a meal. As the α-glucans of the invention display reduced digestibility compared to materials such as starch, meals prepared containing them will cause a reduced blood glucose response compared to the equivalent meal with starch, and will provoke a lower insulin response. A composition comprising the α-glucan of the invention may be for use in the control of postprandial blood glucose and insulin levels in a subject. The subject may be a human or a pet. A composition comprising the α-glucan of the invention may be for use in the treatment or prevention of a disorder linked to an increase in postprandial blood glucose and insulin levels in a subject. The disorder may be selected from the group consisting of diabetes, for example gestational diabetes; impairment of glucose metabolism; hyperinsulinemia or insulin resistance. The subject may be a diabetic or pre-diabetic human or pet.

Typically, postprandial hyper-insulinemia may promote the development of insulin resistance, metabolic syndrome, glucose intolerance and type-2 diabetes [Kopp W., Metabolism. 2003, July; 52(7):840-844]. Lowering the insulin demand after a meal however, can reduce on one hand the deterioration of the glycemic control in type-2 diabetes and on the other hand reduce the risk of developing type-2 diabetes in predisposed subjects.

A "pre-diabetic patient" is a subject showing insulin resistance or impaired glucose metabolism and is predisposed, for example by family history, lifestyle or genetics, for developing diabetes later in life. Reducing insulin secretion reduces the risk of the pancreas becoming exhausted in the long term, and so is beneficial for management of the pancreas in pre-diabetes or patients with metabolic disorders. The use of a composition comprising the α-glucan of the invention would consequently reduce the risk and/or the development of diabetes, impaired glucose metabolism, hyperinsulinemia or insulin resistance in those subjects.

Prevalence of diabetes, insulin resistance or glucose intolerance is mostly observed in adult humans. However, more and more children are affected, or predisposed or at risk of developing such a disorder later in life. Hence, advantageously, prevention and/or treatment of those disorders is started already in young age. Alternatively, and similarly as observed with humans; diabetes, hyperinsulinemia or insulin resistance are more and more widespread among animals, particularly with animals kept as pet animals. Hence, the invention also pertains to cats and dogs.

A composition comprising the α-glucan of the invention may be for non-therapeutic use to decrease plasma postprandial glucose and insulin levels. It is advantageous that a composition comprising the α-glucan of the invention can also be administered to subjects, for example healthy subjects, which may be at risk of developing diabetes type-2, insulin resistance or glucose intolerance at some later time. A composition comprising the α-glucan of the invention, as disclosed herein, provides a reduced insulin level after consumption. Many healthy people desire to lose weight. Consuming meals which contain dietary fibre can increase satiety and therefore help people consume fewer digestible calories. A composition comprising the α-glucan of the invention may be for non-therapeutic use to lose weight.

Another aspect of the invention relates to a food composition comprising the α-glucan of the invention. The α-glucan of the invention provides a carbohydrate with low digestibility but yet a good solubility, making it ideal for use in food products where a reduced calorie content is required. The food composition may be a beverage, for example a powdered beverage mix or a beverage creamer; a breakfast cereal; a pet food product; a baked dough product, for example a bread, a pizza or a filled savoury turnover; or a confectionery product. The confectionery product may be a frozen confectionery product such as an ice-cream; a baked confectionery product such as a biscuit, for example a filled biscuit or wafer; a chocolate confectionery product; or a sugar-style confectionery product such as a gum, a jelly, a hard-boiled sweet or a chewy sweet. The term sugar-style confectionery product or sugar-style candy refers to confectionery products which would traditionally have been based on sugar, but may be manufactured with alternative sweeteners and/or sugar substitutes.

In a further embodiment, the invention provides for the use of an α-glucanotransferase enzyme that comprises an amino acid sequence having at least 90% identity to SEQ ID NO:1 (for example at least 92, 95, 96, 97, 98, or 99% identity to SEQ ID NO:1), or has the amino acid sequence of SEQ ID NO:1, for reducing the digestible carbohydrates of a food material, for example a starch-containing food material. In the scope of the current invention, digestible carbohydrates correspond to the fraction of the total carbohydrates that is digestible and available to provide energy to body cells. The α-glucanotransferase enzyme used according to the invention may be a *Lactobacillus fermentum* CNCM I-5068 GTFB enzyme.

A still further embodiment of the invention is a bacteria comprising a nucleic acid sequence having at least 90% identity to SEQ ID NO:2 (for example at least 92, 95, 96, 97, 98, or 99% identity to SEQ ID NO:2), or has the nucleic acid sequence of SEQ ID NO:2. The bacteria comprising the nucleic acid sequence identified by SEQ ID NO:2 may be a *Lactobacillus fermentum*, for example *Lactobacillus fermentum* CNCM I-5068.

An embodiment of the invention is *Lactobacillus fermentum* CNCM I-5068, also named NCC 2970. It was deposited with the Collection Nationale de Cultures de Microorganismes (CNCM), Institut Pasteur, 25 rue du Docteur Roux, F-75724 PARIS Cedex 15, France, on 8 Mar. 2016 and given the deposit number I-5068.

*Lactobacillus fermentum* CNCM I-5068 may be grown in a fermentation broth, optimizing the conditions to maximize production of the GTFB enzyme. The optimum conditions can for example be identified by measuring the expression of the enzyme by real-time polymerase chain reaction (PCR). Conversion of a polysaccharide or oligosaccharide substrate such as amylose may then be achieved using the fermentation broth, or by fermenting the *Lactobacillus fermentum* CNCM I-5068 in the presence of the polysaccharide or oligosaccharide substrate. *Lactobacillus fermentum* CNCM I-5068 may conveniently be provided in the form of a freeze-dried powder.

In a further embodiment the invention provides an α-glucanotransferase enzyme comprising an amino acid sequence having at least 90% identity to SEQ ID NO:1, for example an α-glucanotransferase enzyme consisting of an amino acid sequence having at least 90% identity to SEQ ID NO:1. The invention further provides an expression vector comprising a nucleic acid sequence encoding a polypeptide possessing at least 90% sequence identity to SEQ ID NO:1 (for example at least 92, 95, 96, 97, 98, or 99% identity to SEQ ID NO:1). The expression vector may be a vector to transform a bacteria.

Those skilled in the art will understand that they can freely combine all features of the present invention disclosed herein. In particular, features described for the method of the present invention may be combined with the product of the present invention and vice versa. Further, features described for different embodiments of the present invention may be combined. Where known equivalents exist to specific features, such equivalents are incorporated as if specifically referred to in this specification. Further advantages and features of the present invention are apparent from the figures and experimental section.

Experimental Section

Introduction

Glycoside hydrolase family 70 (www.CAZy.org) initially was established to accommodate glucansucrase enzymes converting sucrose into α-glucan polysaccharides, exclusively found in lactic acid bacteria, especially in the genera *Leuconostoc*, *Streptococcus*, *Lactobacillus*, *Weissella* and *Oenococcus*. Depending on the GS specificity, structurally different α-glucans are formed. Initially mostly glucansucrase enzymes synthesizing α-glucans with (α1→3)-(mutan) or (α1→6)-linkages (dextran) were characterized; in recent years also various α-glucans with (α1→2)- or (α1→4)-linkages have been identified as glucansucrase products. A few glucansucrase enzymes have been characterized that produce α-glucans with alternating (α1→3)/(α1→6)-linkages (alternan) (e.g. alternansucrase of *Leuconostoc mesenteroides* NRRL B-1355) or (α1→4)/(α1→6)-linkages (reuteran) (e.g. reuteransucrase of *Lactobacillus reuteri* 121). Also, branching points may be introduced, either by the same enzyme or by separate (α1→2)- or (α1→3)-branching enzymes of *L. mesenteroides* strains. GSs thus are able to synthesize all four possible linkage types of α-glycosidic bonds [(α1→2), (α1→3), (α1→4) and (α1→6)], but certain combinations of glycosidic linkages have been never found within the same α-glucan. For example, no wild-type glucansucrase enzymes synthesizing α-glucans with (α1→3) plus (α1→4)-linkages have been reported so far. The α-glucans produced by GSs also differ in their degree of branching, molecular mass, and conformation. Such differences result in α-glucans showing different functional properties with promising diverse industrial applications.

Family GH70 GS enzymes (acting on sucrose) are evolutionary related to family GH13 α-amylase enzymes (acting on maltodextrins/starch), constituting clan GH-H. Due to their evolutionary relatedness, GH70 and GH13 family enzymes display similarities in their sequence and structure, and use a comparable α-retaining double displacement catalytic mechanism. Both families have a catalytic $(\beta/\alpha)_8$ barrel structure in their proteins, with domains A, B and C, and an active site with 4 conserved regions regarded as sequence fingerprints for the individual enzyme specificities. However, GSs also exhibit unique features. In family GH13 the order of these 4 conserved regions is I-II-III-IV. In contrast, in GS enzymes this $(\beta/\alpha)_8$ barrel is circularly permuted, which results in the conserved region order II-III-IV-I, and they possess two extra and unique domains IV and V. Besides, GSs present a "U-fold" domain structure in which 4 (domains A, B, IV and V) of the 5 domains are built up from two discontinuous segments of the polypeptide chain. During their evolution from GH13, the GH70 enzymes appear to have undergone a sequence of gene rearrangements that resulted in this unusual, circularly permuted domain organization.

In recent years several maltodextrins/starch converting enzymes have been identified within the GH70 family supporting the evolutionary relatedness of GH13 and GH70 families. Firstly, it was found that *L. reuteri* 121 produced a GS-like enzyme that was inactive on sucrose. The gene encoding this enzyme was found upstream of the gene encoding the glucansucrase GTFA and designated as gtfB. Instead of sucrose, the *L. reuteri* 121 GTFB acts on maltodextrins and starch substrates, cleaving (α1→4)-linkages from the non-reducing end of the donor substrate, and synthesizing new (α1→6)-linkages on the non-reducing end of the product (4,6-α-glucanotransferase activity, 4,6-α-GTase). This results in the synthesis of products with linear chains of (α1→6)- and (α1→4)-linkages (isomalto/maltopolysaccharides, IMMP). A total of 54 related GTFB type of enzymes are currently available in databases, with 4 exceptions they are all found in the genus *Lactobacillus*, constituting a new GH70 subfamily. Following the annotation of many new genome sequences, a few family GH70 enzymes also were found in non-LAB genera. Previously the GTFC enzyme of *Exiguobacterium sibiricum* 255-15 [Gangoiti J, Pijning T, Dijkhuizen L., Appl Environ Microbiol 82:756-766. (2015)] and the GTFD enzyme of *Azotobacter chroococcum* NCIMB 8003 [Gangoiti J, van Leeuwen S, Vafiadi C, Dijkhuizen L., Biochem Biophys Act 1860: 1224-1236 (2016)] have been characterized. Both of these enzymes are inactive with sucrose and active with maltodextrins/starch, displaying 4,6-α-GTase activity that resulted in synthesis of isomaltose/maltose oligosaccharides (IMMO) (GTFC) and in a reuteran type of α-glucan (GTFD). Surprisingly, the domain order in GTFC and GTFD resembles that of GH13 enzymes, with a nonpermuted order of conserved regions I-II-III-IV, and lacking domain V found in other GH70 enzymes. GTFC and GTFD represent 2 additional GH70 subfamilies and are structurally very interesting evolutionary intermediates between GH13 α-amylase and GH70 glucansucrase enzymes, allowing further analysis of the evolutionary origins and differentiation of the (sub)families in clan GH-H (http://www.cazy.org).

Annotation of the *Lactobacillus fermentum* NCC 2970 genome sequence resulted in identification of a single family GH70 protein with clear sequence similarity to the GTFB-type of 4,6-α-GTase enzymes. It also had all features of a typical 4,6-α-GTase enzyme, being inactive with sucrose and active with maltodextrins/starch. However, the *Lb. fermentum* GTFB amino acid sequence showed unique variations in some of the residues in conserved regions II and IV, contributing to the active site donor/acceptor substrate binding subsites. The inventors therefore decided to biochemically characterize this *L. fermentum* GTFB enzyme, including a detailed characterization of its products. This revealed that it possesses 4,3-α-glucanotransferase (4,3-α-GTase) activity with maltodextrins/starch, a novel reaction specificity in family GH70 and clan GH-H.

Materials and Methods
*L. fermentum* GTFB Protein Sequence Analysis

Analysis of the *Lactobacillus fermentum* NCC 2970 genome (SEQ ID NO:2) by BLAST using the *L. reuteri* 121 GTFB (GenBank accession no. AAU08014.2) as query sequence allowed the identification of a GH70 protein encoding gene. Sequences showing similarity to the *L. fermentum* GH70 protein sequence were found using NCBI BLASTp searches (http://www.ncbi.nlm.nih.gov/BLAST/) against the non-redundant protein sequence database. Multiple amino acid sequence alignments were made with Clustal W2 using Jalview 2 desktop application. The presence of a signal peptide was analyzed using the Signal P4 server. Subcellular localization of the *L. fermentum* GTFB protein was predicted using CELLO v.2.5: subCELlular LOcalization predictor (http://cello.life.nctu.edu.tw/). The theoretical Mw (molecular weight) of the GTFB protein was predicted on ExPASy Compute pI/Mw (http://web.expasy.org/compute_pi/).

Phylogenetic analysis was performed using MEGA, version 6 (Tamura et al., 2013) with a total of 72 amino acid sequences corresponding to representative characterized GH70 proteins indexed in CAZy and GTFB-like protein sequences identified via BLASTp. Sequences were aligned by MUSCLE, using default parameters. A phylogenetic tree was constructed by the Maximum Likelihood method based on the HT matrix model using MEGA6. Partial deletion of the positions containing alignment gaps and missing data was conducted. Statistical confidence of the inferred phylogenetic relationships was assessed by performing 1,000 bootstrap replicates.

Cloning of the *L. fermentum* GTFB Gene

The DNA fragment coding for an N-terminally truncated version of the GTFB protein (amino acids 616-1593) was amplified from *L. fermentum* NCC 2970 chromosomal DNA using Phusion DNA polymerase (Finnzyme, Helsinki, Finland) and cloned into a modified pET15b vector using ligation-independent cloning (LIC). The primers used for amplifying the N-terminally truncated gtfB gene derivative incorporated 5' extensions (underlined) to facilitate the LIC cloning, and were: Forward CAGGGACCCGGTTTTGG-TAAAGATGGTCGGATTG (SEQ ID NO: 3) and Reverse CGAGGAGAAGCCCGGTTAATTGTCTTCAATATTAG-CATAATAATC (SEQ ID NO: 4). The resulting PCR product was purified from the agarose band and digested in the presence of dATP, with the 3' to 5' exonuclease activity of the T4 DNA polymerase (New England Biolabs). In parallel, the pET-15b/LIC vector was digested with KpnI, isolated from gel and then treated with T4 DNA polymerase (New England Biolabs) in the presence of dTTP. The treated pET-15b/LIC vector and the amplicon were mixed together in a 1:4 molar ratio, and the mixture was used to transform *Escherichia coli* DH5a cells (Phabagen). This resulted in a gtfB-ΔN construct containing an N-terminal His6-tag (SEQ ID NO: 85) cleavable by a 3C protease. The constructed expression vector pET15b/gtfB-ΔN was transformed into host *E. coli* BL21 Star (DE3). The gene sequence was verified by nucleotide sequencing (GATC, Cologne, Germany).

Enzyme Expression and Purification

For expression of the *L. fermentum* GTFB enzyme, an *E. coli* star BL21 (DE3) overnight culture, transformed with pET15b/gtfB-ΔN was diluted 1:100 into fresh LB broth supplemented with ampicillin (100 μg ml$^{-1}$) and grown at 37° C. and 220 rpm until the optical density at 600 nm reached approximately 0.4. The temperature for culturing was then decreased to 16° C., and the inducer isopropyl-β-D-1-thiogalactopyranoside was added to a final concentration of 0.1 mM. After 20 h, cells were harvested by centrifugation (10,000 g×20 min), and subsequently disrupted with B-PER lysis reagent in accordance to the protocol described by the manufacturer (Thermo Scientific, Pierce). The recombinant GTFB protein was isolated from the cell-free extract by His-tag affinity chromatography using Ni$^{2+}$-nitrilotriacetate (Ni-NTA) as column material (Sigma-Aldrich). After washing the column with 25 mM Tris-HCl (pH 8.0), 1 mM CaCl$_2$, bound proteins were eluted with 200 mM imidazole in the same buffer and the imidazole was removed by use of a stirred ultrafiltration unit (Amicon, Beverly, Mass.) with a 30,000 molecular weight cut off. For further purification, the protein was loaded on a 1 ml-HiTrap column (GE Healthcare) and eluted (at a 1-ml/min flow rate) using a linear gradient of NaCl (from 0 to 1 M) in 20 mM Tris-HCl buffer (pH 8.0), containing 1 mM CaCl$_2$. Fractions of 1 ml were collected using an Äkta fast protein liquid chromatograph (FPLC; GE Healthcare, Uppsala, Sweden). The buffer was exchanged by ultrafiltration (YM30 membranes; Millipore, Billerica, Mass.). The purification progress was assessed by SDS-PAGE analysis of the fractions, and the protein concentrations were determined using a Nanodrop 2000 spectrophotometer (Isogen Life Science, De Meern, The Netherlands).

Enzyme Activity Assays

The initial total activity of the *L. fermentum* GTFB-ΔN enzyme was determined by the amylose-iodine method [Gangoiti J, Pijning T, Dijkhuizen L., Appl Environ Microbiol 82:756-766. (2015)][Bai Y, van der Kaaij R M, Leemhuis H, Pijning T, van Leeuwen S S, Jin Z, Dijkhuizen L., 2015. Appl Environ Microbiol 81:7223-7232. (2015)]. The decrease in absorbance of the α-glucan-iodine complex resulting from transglycosylation and/or hydrolytic activity was monitored at 660 nm for 14 min at 40° C. The reaction mixture contained 0.125% (w v$^{-1}$) amylose V (AVEBE, Foxhol, The Netherlands), 2.5 μg ml$^{-1}$ of enzyme, 25 mM sodium acetate (pH 5.5) and 1 mM CaCl$_2$. One unit of activity was defined as the amount of enzyme converting 1 mg of substrate per min.

The effect of pH on enzyme activity was determined at 40° C. by varying the pH between 3.5 and 8.0. Sodium citrate buffer (25 mM) was used for pH values between 3.5 and 7.0, and sodium phosphate buffer (25 mM) for pH values between 7.0 and 8.0. The optimal temperature was determined in 25 mM sodium citrate buffer, pH 5.5, 1 mM CaCl$_2$, at temperatures ranging from 30 to 65° C. The effect of temperature on GTFB-ΔN stability was determined by incubating the enzyme at a concentration of 0.1 mg ml$^{-1}$ in 20 mM Tris-HCl buffer (pH 8.0) with 1 mM CaCl$_2$, at temperatures from 30 to 55° C. for 10 min. Samples were then immediately cooled to 4° C., and the residual activity was measured under the standard reaction conditions in 25 mM sodium citrate (pH 5.5) with 1 mM CaCl$_2$ at 40° C.

Substrate Utilization by *L. fermentum* GTFB

*L. fermentum* GTFB-ΔN (25 μg ml$^{-1}$) was separately incubated with 25 mM sucrose (Acros), nigerose (Sigma-Aldrich), panose (Sigma-Aldrich), isomaltose (Sigma-Aldrich), isomaltotriose (Sigma-Aldrich), isomaltopentaose (Carbosynth), malto-oligosaccharides (MOS) with degrees of polymerization (DP) 2-7, and 0.6% (w/v) amylose V (AVEBE, Foxhol, The Netherlands), potato starch (Sigma-Aldrich) and amylopectin (Sigma-Aldrich). All reactions were performed in 25 mM sodium acetate buffer (pH 5.5) with 1 mM CaCl$_2$ at 37° C. for 24 h. Reactions were stopped by 6 min of incubation at 100° C. The progress of the reactions was monitored by thin-layer chromatography (TLC) and/or high-performance-anion-exchange chromatography (HPAEC).

Thin Layer Chromatography and High Performance Anion Exchange Chromatography with Pulsed Amperometric Detection Analysis Thin layer chromatography (TLC) was performed on silica gel 60 F254, 20×20 cm TLC sheets (Merck, Darmstadt, Germany). The TLC plates were developed in n-butanol:acetic acid:water (2:1:1, v/v) solvent system for 6 h. The carbohydrates were visualized with orcinol/sulfuric acid staining and compared with a simultaneous run of a mixture of glucose and MOS (DP2 to DP7).

Carbohydrate samples were diluted 3:100 in DMSO and analyzed by HPAEC on a Dionex DX500 workstation (Dionex, Amsterdam, The Netherlands), equipped with a CarboPac PA-1 column (Dionex; 250×2 mm) and a ED40 pulsed amperometric detection system. A gradient of sodium acetate from 10 to 240 mM in 100 mM NaOH was applied over 57 min at 0.25 ml min$^{-1}$ flow rate. The injection volume of each sample was 5 µl. The identity of the peaks was assigned using commercial oligosaccharide standards.

HPSEC Analysis

HPSEC analyses of the products mixtures were performed using a size exclusion chromatography system (Agilent Technologies 1260 Infinity) equipped with a multi angle laser light scattering detector (SLD 7000 PSS, Mainz), a viscometer (ETA-2010 PSS, Mainz) and a differential refractive index detector (G1362A 1260 RID Agilent Technologies), [Gangoiti J, van Leeuwen S, Vafiadi C, Dijkhuizen L., Biochem Biophys Act 1860: 1224-1236. (2016)]. Separation was carried out by using three PFG-SEC columns with porosities of 100, 300 and 4000 Å, coupled with a PFG guard column. DMSO-LiBr (0.05 M) was used as eluent at a flow rate of 0.5 ml min$^{-1}$. The system was calibrated and validated using a standard pullulan kit (PSS, Mainz, Germany) with $M_w$ ranging from 342 to 805 000 Da. The specific RI increment value dn/dc was also measured by PSS and was 0.072 ml g$^{-1}$. The multiangle laser light scattering signal was used to determine the molecular masses of the amylose V and the polymer generated by the L. fermentum GTFB-ΔN enzyme. The specific RI increment value, dn/dc for these polysaccharides in this system was taken to be the same as for pullulan. The molecular mass of the L. reuteri GTFB-ΔN polymer was determined by universal calibration method. WinGPC Unity software (PSS, Mainz) was used for data processing. Measurements were performed in duplicate.

Production, Isolation and Characterization of the Products Synthesized by L. fermentum GTFB from Amylose Purified GTFB-ΔN (0.25 mg) was incubated with amylose V for 48 h at 37° C. under the conditions described above in "Substrate utilization by L. fermentum GTFB". The product mixture obtained was fractionated by size-exclusion chromatography on a BioGel P2 column (2.5×50 cm; Bio-Rad, Veenendaal, The Netherlands) using 10 mM NH$_4$HCO$_3$ as eluent at a flow rate of 48 ml h$^{-1}$. The poly-/oligosaccharides present in the different Biogel P2 pools were analyzed by matrix-assisted laser-desorption ionization time-of-flight mass spectrometry (MALDI-TOF-MS), nuclear magnetic resonance (NMR) spectroscopy and methylation analysis.

(i) MALDI-TOF Mass Spectrometry

MALDI-TOF-MS measurements were recorded on an Axima™ mass spectrometer (Shimadzu Kratos Inc., Manchester, UK) equipped with a nitrogen laser (337 nm, 3 ns pulse width). Sample solutions (1 µL) were spotted on a MALDI target and mixed immediately with 1 µL of aqueous 10% (w v$^{-1}$) 2,5-dihydroxybenzoic acid matrix solution. Positive-ion mode spectra were recorded using the reflector mode at a resolution of 5000 Full Width at Half Maximum (FWHM) and delayed extraction (450 ns). Mass spectra were generally acquired from 1 to 5000 Da with ion-gate blanking at 200.

(ii) NMR Spectroscopy

One- and two-dimensional $^1$H nuclear magnetic resonance (NMR) spectra were recorded on a Varian Inova 500 spectrometer (NMR Center, University of Groningen), using D$_2$O as solvent and at a probe temperature of 298K. Prior to analysis, samples were exchanged twice in D$_2$O (99.9 atom % D, Cambridge Isotope Laboratories, Inc., Andover, Mass.) with intermediate lyophilization, and then dissolved in 0.6 mL of D$_2$O. All NMR spectra were processed with MestReNova 5.3 (Mestrelabs Research SL, Santiago de Compostella, Spain). Chemical shifts (δ) were expressed in ppm and calibrated with the internal standard acetone (δ 2.225 ppm for $^1$H and δ 31.07 for $^{13}$C). The percentage of different linkages was estimated by integration of the respective signal peak areas.

(iii) Methylation Analysis

Methylation analysis was performed as described previously [van Leeuwen S S, Kralj S, van Geel-Schutten I H, Gerwig G J, Dijkhuizen L, Kamerling J P., Carbohydr Res 343:1237-1250. (2008)]. Briefly, the polymer and oligosaccharides samples (~5 mg) were per-methylated using CH$_3$I and solid NaOH in DMSO, and subsequently hydrolyzed with trifluoroacetic acid. Partially methylated monosaccharides were reduced with NaBD$_4$. The resulting partially methylated alditols were per-acetylated using pyridine:acetic anhydride (1:1 v/v) at 120° C. yielding mixtures of partially-methylated alditol acetates (PMAAs). PMAAs were analyzed by GLC-EI-MS and GLC-FID as described in van Leeuwen et al., 2008.

Smith Degradation

Samples of 1-2 mg polysaccharide were dissolved in 1 mL 50 mM NaIO$_4$ in 100 mM NaOAc (pH 4.1) and stirred for 112 h at 4° C. in the dark. Excess 104 was neutralised by adding 300 µL ehtyleneglycol. The degraded product was dialysed in a SpectraPor 1000 Da cut-off dialysis floater against running tap water for 48 h. After dialysis the sample was reduced with NaBH$_4$ at room temperature overnight, followed by dialysis as described above. The reduced polysaccharide sample was lyophilized and hydrolysed in 1 mL 90% formic acid at 90° C. for 30 min. After cooling to room temperature formic acid was evaporated by N2 stream. The dried polysaccharide fragments were analysed as TMS derivatives on GLC-EI-MS and GLC-FID, and by HPAEC-PAD as described by Van Leeuwen et al., 2008.

L. fermentum GTFB Product Analysis with Hydrolytic Enzymes

L. fermentum GTFB-ΔN polymer was dissolved at a concentration of 5 mg ml$^{-1}$ in 50 mM sodium acetate buffer pH 5.0, and incubated separately with an excess of α-amylase (Aspergillus oryzae; Megazyme), dextranase (Chaetomium erraticum; Sigma-Aldrich), and pullulanase M1 (Klebsiella planticola; Megazyme) for 48 h at 37° C. Starch, IMMP L. reuteri 121 GTFB polymer and A. chroococcum reuteran-like GTFD polymer, were used as positive controls for the α-amylase, dextranase and pullulanase treatments, respectively, resulting in complete degradation under these conditions. The degree of hydrolysis was examined by TLC analysis.

Results and Discussion

*L. fermentum* GTFB Protein Sequence Analysis

Annotation of the *L. fermentum* genome resulted in identification of a single GH70 family protein. BLASTp analysis of the *L. fermentum* GH70 protein revealed that the closest homologs of this protein all were members of the GTFB-like 4,6-α-GTase GH70 subfamily with more than 47% identical amino acid sequences (Table 1).

TABLE 1

Protein sequences identified via a BLASTp search using the *L. fermentum* NCC 2970 GH70 protein as query. The sequence corresponding to the *L. reuteri* 121 GTFB 4,6-α-glucanotransferase is highlighted in bold.

| NCBI protein names | Organism | Coverage | Identity | Length | Accession |
| --- | --- | --- | --- | --- | --- |
| dextransucrase | *Lactobacillus fermentum* | 100% | 79% | 1478 | WP_046948074.1 |
| Dextransucrase | *Lactobacillus reuteri* mlc3 | 99% | 66% | 1488 | WP_019251413.1 |
| Dextransucrase | *Lactobacillus reuteri* JCM 1112 | 99% | 66% | 1488 | WP_003668618.1 |
| Dextransucrase | *Lactobacillus reuteri* DSM 20016 | 87% | 66% | 1363 | ABQ83597.1 |
| Dextransucrase | *Lactobacillus sanfranciscensis* DSM 20451 | 86% | 69% | 1151 | KRM78746.1 |
| Dextransucrase | *Lactobacillus fermentum* ATCC 14931 | 86% | 79% | 1014 | WP_003683900.1 |
| dextransucrase | *Lactobacillus fermentum* 28-3-CHN | 78% | 78% | 986 | WP_004563243.1 |
| glycosyl hydrolase family 70 | *Lactobacillus delbrueckii* subsp. *Delbrueckii* | 66% | 73% | 1294 | WP_057717954.1 |
| inactive glucansucrase | *Lactobacillus salivarius* GJ-24 | 60% | 88% | 1626 | EGM52218.1 |
| Dextransucrase | *Lactobacillus delbrueckii* subsp. *Lactis* | 66% | 73% | 1294 | WP_013439942.1 |
| glycosyl hydrolase family 70 | *Lactobacillus salivarius* GJ-24 | 53% | 88% | 852 | WP_050809355.1 |
| glycosyl hydrolase family 70 | *Lactobacillus delbrueckii* subsp. *Lactis* DSM 20072 | 62% | 76% | 1252 | WP_057727099.1 |
| glycosyl hydrolase family 70 | *Lactobacillus plantarum* AG30 | 57% | 81% | 932 | WP_033607967.1 |
| glycosyl hydrolase family 70 | *Lactobacillus delbrueckii* subsp. *Lactis* DSM 20072 | 59% | 78% | 1210 | WP_035182758.1 |
| glycosyl hydrolase family 70 | *Lactobacillus delbrueckii* subsp. *Lactis* DSM 20072 | 58% | 80% | 997 | WP_025895575.1 |
| glycosyl hydrolase family 70 | *Lactobacillus plantarum* subsp. *argentoratensis* DSM 16365 | 55% | 84% | 908 | WP_057717369.1 |
| dextransucrase | *Lactobacillus plantarum* subsp. *argentoratensis* DSM 16365 | 54% | 85% | 880 | KRL97820.1 |
| glycosyl hydrolase family 70 | *Lactobacillus delbrueckii* subsp. *bulgaricus* NDO2 | 56% | 83% | 954 | WP_035171046.1 |
| glycosyl hydrolase 70 family protein | *Lactobacillus delbrueckii* subsp. *lactis* CRL581 | 54% | 85% | 922 | EPB98082.1 |
| glycosyl hydrolase family 70 | *Lactobacillus plantarum* WLPL04 | 56% | 82% | 922 | WP_057138784.1 |
| glycosyl hydrolase 70 family protein | *Pediococcus pentosaceus* IE-3 | 57% | 81% | 926 | WP_002833996.1 |
| glycosyl hydrolase family 70 | *Lactobacillus delbrueckii* KACC 13439 | 56% | 83% | 965 | WP_052933722.1 |
| glycosyl hydrolase family 70 | *Lactobacillus delbrueckii* subsp. *delbrueckii* KACC 13439 | 54% | 85% | 922 | KNZ37797.1 |
| cell wall-binding repeat protein | *Lactobacillus delbrueckii* subsp. *bulgaricus* PB2003/044-T3-4 | 58% | 80% | 957 | EFK31460.1 |
| Dextransucrase | *Pediococcus pentosaceus* DSM 20336 | 53% | 85% | 874 | KRN47461.1 |
| glycosyl hydrolase family 70 | *Lactobacillus delbrueckii* JCM 17838 | 54% | 85% | 922 | WP_050952694.1 |
| glycosyl hydrolase family 70 | *Lactobacillus delbrueckii* subsp. *lactis* | 57% | 85% | 922 | WP_035162295.1 |
| glycosyl hydrolase family 70 | *Pediococcus pentosaceus* DSM 20336 | 54% | 84% | 883 | WP_056979574.1 |
| Dextransucrase | *Lactobacillus delbrueckii* subsp. *jakobsenii* ZN7a-9 = DSM 26046 | 54% | 80% | 966 | WP_002879779.1 |
| glycosyl hydrolase family 70 | *Lactobacillus delbrueckii* subsp. *jakobsenii* ZN7a-9 = DSM 26046 | 53% | 80% | 948 | WP_057709472.1 |
| glycosyl hydrolase family 70 | *Lactobacillus mucosae* LM1 | 53% | 84% | 881 | WP_053069107.1 |
| Dextransucrase | *Lactobacillus delbrueckii* subsp. *jakobsenii* ZN7a-9 = DSM 26046 | 53% | 85% | 895 | KR017768.1 |
| glycosyl hydrolase family 70 | *Leuconostoc mesenteroides* 406 | 53% | 85% | 850 | WP_059442690.1 |
| inactive glucansucrase | ***Lactobacillus reuteri* 121 | 57% | 77% | 1619 | AAU08014.2** |
| putative glucansucrase | *Lactobacillus reuteri* ML1 | 59% | 77% | 1620 | AAU08003.2 |
| FIG00744899: hypothetical protein | *Lactobacillus reuteri* pg-3b | 62% | 76% | 1622 | CUR36485.1 |
| hypothetical protein HQ33_10125 | *Lactobacillus reuteri* TMW1.656 | 59% | 77% | 1602 | KOF04763.1 |
| putative glucansucrase | *Lactobacillus reuteri* TMW1.106 | 53% | 77% | 1383 | ABP88725.1 |
| putative dextransucrase | *Lactobacillus plantarum* 16 | 86% | 52% | 1348 | WP_016526729.1 |

TABLE 1-continued

Protein sequences identified via a BLASTp search using the L. fermentum NCC 2970 GH70 protein as query. The sequence corresponding to the L. reuteri 121 GTFB 4,6-α-glucanotransferase is highlighted in bold.

| NCBI protein names | Organism | Coverage | Identity | Length | Accession |
| --- | --- | --- | --- | --- | --- |
| hypothetical protein | Lactobacillus sanfranciscensis DSM 20451 | 57% | 67% | 924 | WP_056958823.1 |
| inactive glucansucrase | Lactobacillus panis DSM 6035 | 57% | 67% | 1603 | KRM25865.1 |
| hypothetical protein | Pediococcus argentinicus DSM 23026 | 53% | 70% | 898 | WP_057799472.1 |
| Dextransucrase | Pediococcus argentinicus DSM 23026 | 53% | 70% | 890 | KR024973.1 |
| Dextransucrase | Lactobacillus paraplantarum DSM 10667 | 57% | 65% | 920 | KRL44364.1 |
| hypothetical protein | Lactobacillus plantarum NL42 | 57% | 65% | 907 | WP_052697219.1 |
| Dextransucrase | Lactobacillus paraplantarum DSM 10667 | 57% | 65% | 929 | WP_056988774.1 |
| hypothetical protein | Lactobacillus plantarum CI P104448 | 69% | 47% | 1266 | WP_052661628.1 |
| hypothetical protein | Lactobacillus acidipiscis KCTC 13900 | 63% | 49% | 1567 | WP_050955745.1 |
| hypothetical protein | Lactobacillus acidipiscis DSM 15353 | 60% | 51% | 1139 | WP_056988183.1 |
| dextransucrase | Lactobacillus acidipiscis DSM 15353 | 60% | 51% | 1143 | KRN79505.1 |
| Dextransucrase | Lactobacillus aviarius subsp. aviarius DSM 20655 | 99% | 50% | 1567 | KRM39240.1 |

Figure 1:
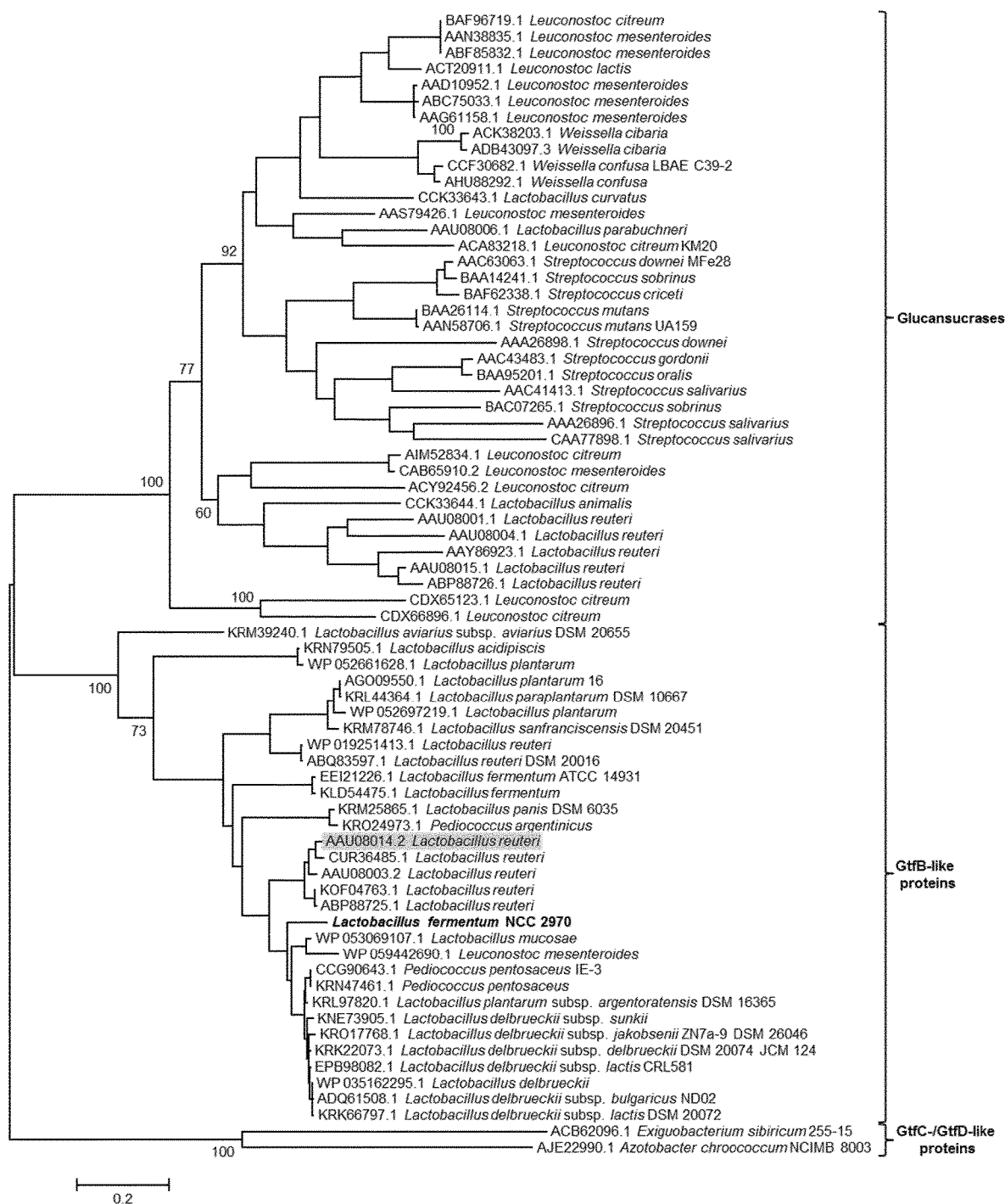
FIG. 1 shows a phylogenetic tree constructed on the basis of complete amino acid sequence alignment of some of the characterized GH70 proteins annotated in the CAZy database (http://www.CAZy.org), and of (putative) GH70 GTFB-like proteins identified by a BLAST search using the *L. fermentum* GH70 NCC 2970 protein as query sequence (shown in bold). The evolutionary history was inferred by using the Maximum Likelihood method based on the JTT matrix-based model. The bar represents a genetic distance of 0.2 substitutions per position (20% amino acid sequence difference). The bootstrap values adjacent to the main nodes represent the probabilities based on 1000 replicates. The protein sequences are annotated by their Genbank accession number and bacterial origin. The *L. reuteri* 121 GTFB 4,6-α-GTase is highlighted with a grey background.

The phylogenetic relationship of the L. fermentum GH70 protein to other characterized GH70 enzymes and (putative) GH70 4,6-α-GTases identified by this BLASTp search is depicted in FIG. 1. Glucansucrases (GSs) are present in the genomes of lactic acid bacteria of the genera Leuconostoc, Streptococcus, Lactobacillus, Oenococcus and Weissella, but most genes encoding putative GTFB homologs are currently found in Lactobacillus strains (except 4 GTFB-like proteins present in Pediococcus and Leuconostoc strains). The L. fermentum GH70 enzyme clustered together with the L. reuteri 121 GTFB 4,6-α-GTase and its homologs, indicating that this protein is a member of the GTFB-type of GH70 subfamily. The GTFB-like proteins display a domain organization resembling that of GH70 GSs with a circularly permuted $(\beta/\alpha)_8$ barrel, however, biochemically they are more related to the E. sibiricum 255-15 GTFC and A. chroococcum NCIMB 8003 GTFD enzymes. In agreement with these observations, the GTFB-like GH70 subfamily is evolutionary more closely related to GSs, but it has an intermediate position between the GSs and the GTFC and GTFD 4,6-α-GTases encoded by E. sibiricum 255-15 and A. chroococccum NCIMB 8003.

Figure 3:
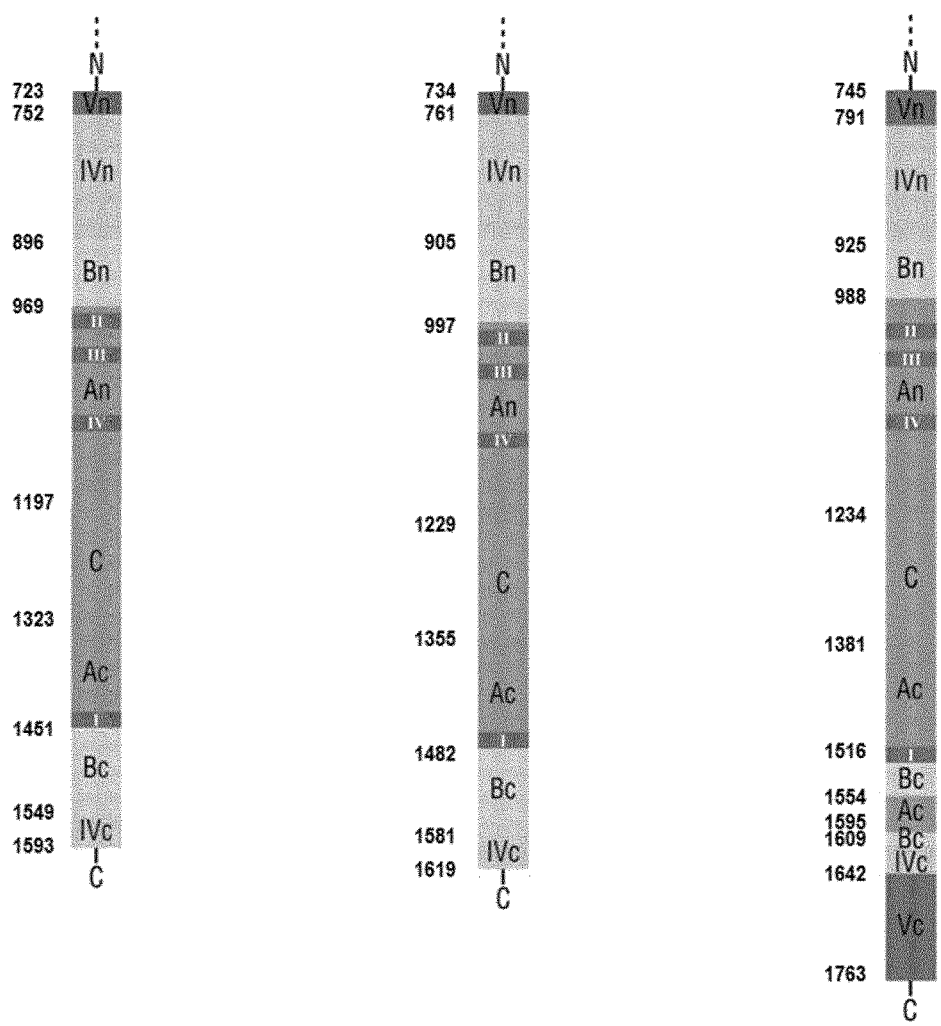
FIG. 3 shows a schematic representation of the domain arrangement along the polypeptide chains of *L. fermentum* GTFB 4,3-α-glucanotransferase, *L. reuteri* 121 GTFB-ΔN 4,6-α-glucanotransferase and *L. reuteri* 121 GTFA glucansucrase. Domains A, B, C, IV and V were identified in the *L. fermentum* GTFB primary structure by sequence comparisons with the *L. reuteri* 121 GTFB and GTFA sequences, using Clustal W2.

The identified GTFB gene sequence from L. fermentum encodes a polypeptide consisting of 1593 amino acids with a calculated molecular mass of 180 kDa. In agreement with the extracellular location of GH70 enzymes, the L. fermentum GTFB was predicted to function as an extracellular protein by the CELLO v.2.5: subCELlular LOcalization predictor server. Analysis of the N-terminus of the amino acid sequence of L. fermentum GTFB using the algorithm of the Signal P 4.0 server revealed that this protein contains the classical Gram-positive N-terminal signal peptide of 39 amino acids. The L. fermentum GTFB shares significant amino acid identity (77% identity, 57% coverage) with the L. reuteri 121 GTFB, the first characterized GH70 member with 4,6-α-glucanotransferase activity (EP2248907). Besides, the typical U-fold domain organization characteristic of most GH70 proteins consisting of five domains (A, B, C, IV and V), is also found in the L. fermentum GTFB enzyme (FIG. 3). Similar to L. reuteri 121 GTFB, domains A, B, C and IV of the L. fermentum GTFB protein are built up from discontinuous N- and C-terminal stretches of the polypeptide chain, whereas domain V only consists of an N-terminal polypeptide segment. Besides, the L. fermentum GTFB has a large variable N-terminal domain of ~700 residues present in many glucansucrases and GTFB-like proteins of Lactobacillus species that is believed to be involved in cell wall attachment [Bath K, Roos S, Wall T, Jonsson H. FEMS Microbiol Lett 253:75-82. (2005)].

Aiming to predict the reaction and/or product specificity of the L. fermentum GTFB enzyme, the homology regions I-IV of this protein were identified by sequence alignments with other GH70 family proteins (FIG. 2). These four homology motifs contain the catalytic and substrate-binding residues, and thus, are regarded as sequence fingerprints for the individual enzyme specificities in both GH70 and GH13 family enzymes. The order of the conserved regions I-IV in the L. fermentum GTFB is II-III-IV-I and corresponds to the order found in glucansucrases and GTFB-like 4,6-α-glucanotransferases, reflecting its circularly permuted domain organization. Motifs I-IV of the L. fermentum GTFB showed significant similarities with those corresponding to (putative) GTFB-like 4,6-α-glucanotransferases. First, the seven residues strictly conserved in motifs I-IV of GH70 family enzymes are present in the L. fermentum GTFB. Among these seven residues, the three putative catalytic residues Asp987, Glu1025 and Asp1097 (L. fermentum GTFB numbering), were identified as the nucleophile, the general acid/base catalyst and the transition state stabilizer, respectively. Similar to other GTFB-like enzymes, a Tyr residue replaces the subsite +1/+2 Trp residue (W1065 in L. reuteri GTF180 GS) conserved in all GSs, except for the branching sucrases. It is noteworthy that the conserved W1065 (GTF180 L. reuteri 180 numbering) is also substituted by a Tyr in the E. sibiricum GTFC and A. chroococcum GTFD 4,6-α-GTase enzymes. Thus, the presence of a Tyr residue at this position instead of the typical Trp residue represents one the main differences discriminating a GH70 protein active on starch/maltodextrin substrates from "classical" GSs. Also, *L. fermentum* GTFB contains Asp and Arg residues at positions 1028 and 1138 (GTF180 *L. reuteri* 180 numbering) contributing to the substrate-binding subsites+1 and +2, respectively, as is the case in most GTFB-like 4,6-α-GTases. However, the *L. fermentum* GTFB also shows unique variations in some of the residues contributing to the −1, +1, and +2 donor/acceptor binding subsites in motifs II and IV. Specifically, subsite+1 Asn residue (N1029 in *L. reuteri* GTF180 GS), which is highly conserved in glucansucrases and GTFB-like proteins, is replaced by an Asp in *L. fermentum* GTFB. In GSs, residue N1019 was found to be essential for activity and linkage specificity. Besides, the amino acids at positions 1137 and 1140 following the putative transition state stabilizer (GTF180 *L. reuteri* 180 numbering), are Ile and Asn, instead of the Gln and Lys residues present in most GTFB- and GTFC-like 4,6-α-GTases. Previous mutational studies revealed that these two residues contribute to glycosidic linkage specificity in GSs. In particular, the residue at position 1137 was found to be critical for the correct orientation of the sugar moiety at subsite +2. Despite the fact that the *L. fermentum* GTFB exhibits clear sequence similarity with the *L. reuteri* 121 GTFB 4,6-α-GTase protein, it contains unique sequence features in functionally important positions.

Purification and Biochemical Characterization of the *L. fermentum* GTFB

Figure 4:
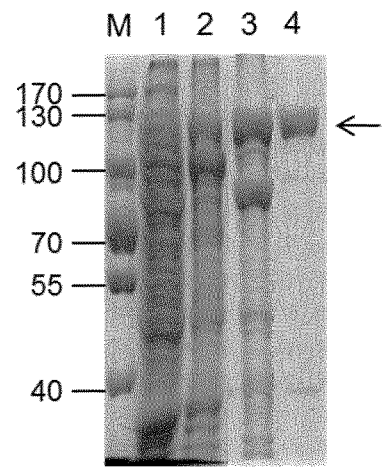
FIG. 4 shows an SDS-PAGE analysis of *L. fermentum* GTFB GH70 protein samples at different stages of purification. Lane M, molecular mass standards; lane 1, sample of *E. coli* cell free extract; lane 2, sample of the insoluble fraction after centrifugation of lysed cells; lane 3, pooled fractions after Ni-NTA agarose column chromatography; lane 4, purified GTFB 4,3-α-glucanotransferase after anion-exchange Hi-trap column chromatography. Bands corresponding to the *L. fermentum* GTFB protein are marked with an arrow.

The *L. fermentum* GTFB-ΔN protein was successfully expressed in *E. coli* BL21(DE3) Star. Under the growth and inductions conditions used, the expression level of GTFB-ΔN was relatively low in both the soluble and insoluble fractions (FIG. 4). The enzyme was purified from the soluble fraction by two chromatographic steps consisting of metal chelate chromatography and anion-exchange chromatography, as described in the Experimental Section. SDS-PAGE analysis of the purified enzyme revealed a single protein band with an apparent molecular mass of ~110 kDa (FIG. 4) which fits the theoretical value deduced from the sequence. As a result of this purification process, a total of 0.4 mg of pure GTFB-ΔN protein per L of *E. coli* culture was obtained.

Figure 5:
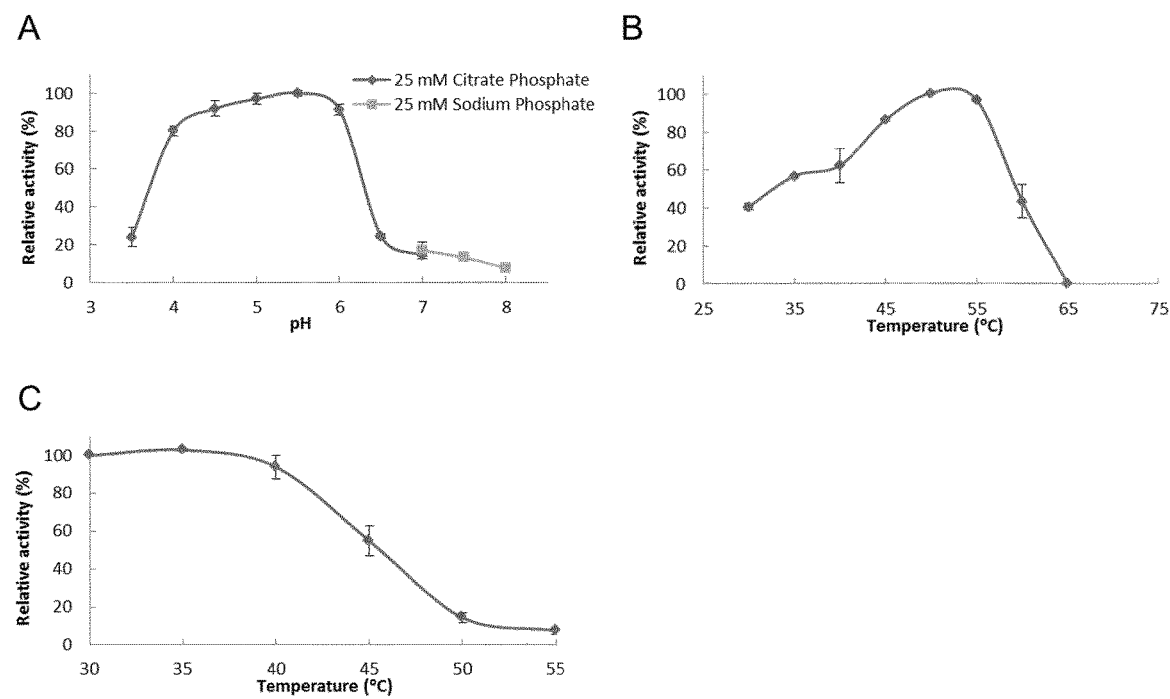
FIG. 5 is a series of graphs showing aspects of the biochemical properties of the purified *L. fermentum* GTFB enzyme. (A) Effect of pH on GTFB activity. Experiments were performed at 40° C. and the relative enzyme activity was compared with that at pH 5.5 (100% value). (B) Effect of temperature on GTFB activity. The assays were carried out at pH 5.5 and relative enzyme activity was compared with that at 50° C. (100% value). (C) Effect of temperature on GTFB stability. GTFB enzyme (0.1 mg ml$^{-1}$) was incubated for 10 min at the indicated temperature in 20 mM Tris-HCl pH 8.0 buffer containing 1 mM CaCl$_2$. Residual activity was assayed at 40° C. using amylose V as substrate under the standard conditions described in the experimental section. Experiments were performed in triplicate, and the bars indicate the standard error of three replicates.

The effects of pH and temperature on the enzyme activity were determined by the iodine-staining assay using amylose V as substrate. The purified recombinant *L. fermentum* GTFB exhibited the highest activity at pH 5.5 and retained more than 80% of this activity over a pH from 4 to 6 (FIG. 5A). The enzyme was active between 30 and 60° C., showing its maximal activity at 50° C., but the activity decreased drastically when the reaction was performed at 65° C. (FIG. 5B). In addition, the enzyme showed low stability at temperatures above 45° C. in 20 mM Tris-HCl buffer pH 8.0 (FIG. 5C). Similar pH and temperature optimum values were reported for the *L. reuteri* 121 GTFB 4,6-α-GTase enzyme. The specific total activity of the purified *L. fermentum* GTFB enzyme on 0.125% (w v$^{-1}$) amylose V in sodium acetate buffer pH 5.5, containing 1 mM CaCl$_2$ was calculated by iodine-staining assay as 22±0.36 U mg$^{-1}$ of protein. This value is around 10 times higher than the one reported for the GTFB from *L. reuteri* 121 (under its optimal conditions of pH 5.0 and 40° C.), namely, 2.8 U mg$^{-1}$ [Bai et al., 2015]. The activity of the *L. fermentum* GTFB was also assayed in the presence of the chelating agent EDTA at a final concentration of 10 mM, resulting in a slight (20%) inhibition.

Substrate and Product Specificity of the *L. fermentum* GTFB

Figure 6:
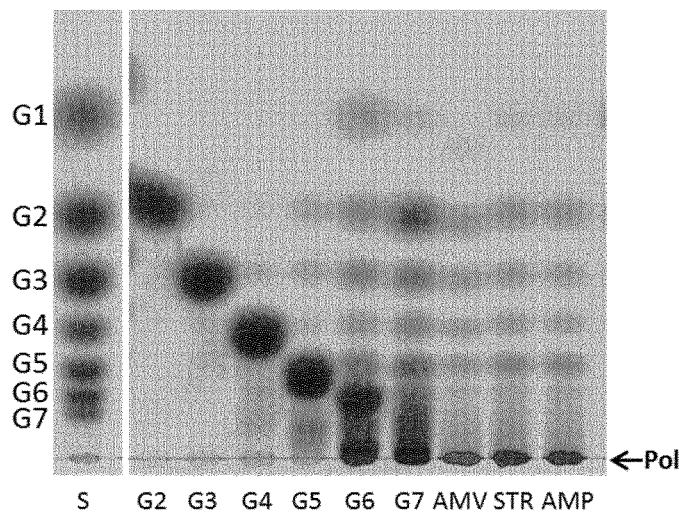
FIG. 6 shows a TLC analysis of the product mixtures synthesized by 25 μg ml$^{-1}$ of the *L. fermentum* GTFB enzyme in incubations with 25 mM malto-oligosaccharides (DP2-DP7), 0.6% (w v$^{-1}$) amylose V, 0.6% (w v$^{-1}$) potato soluble starch, and 0.6% (w v$^{-1}$) amylopectin. The reaction mixtures were incubated at 37° C. and pH 5.5 during 24 h. S, standard; G1, glucose; G2-G7, maltose to maltoheptaose; AMV, amylose V; STR, starch; AMP, amylopectin; Pol, polymer.

The differences observed in the homology motifs suggested that the *L. fermentum* GTFB may possess a new enzymatic reaction and/or product specificity. Therefore the *L. fermentum* GTFB enzyme was incubated with different oligosaccharides and polysaccharides at 37° C. for 24 h, and the reaction products were analysed by TLC (FIG. 6). Similar to *L. reuteri* GTFB, the *L. fermentum* GTFB enzyme failed to act on sucrose, panose, nigerose, and isomalto-oligosaccharides with DP2, DP3, and DP5 (Data not shown). Instead, the *L. fermentum* GTFB enzyme showed both hydrolysis and transglycosylase (disproportionation) activity on malto-oligosaccharides (MOS) of DP 6 and 7, evident from the accumulation of lower- and higher-molecular-mass products than the MOS substrates.

However, *L. fermentum* GTFB was not active on MOS of DP below 4 and showed low disproportionating activity with maltopentaose (DP5); in the case of the *L. reuteri* 121 GTFB activity was already observed with maltotriose (DP3). Incubation of amylose V, potato starch and amylopectin with the *L. fermentum* GTFB enzyme resulted in the appearance of a range of lower molecular mass products indicating that the enzyme was also active on these polymers. It should be noted that the *L. fermentum* GTFB enzyme produced significantly larger amounts of oligosaccharide products than the *L. reuteri* 121 GTFB, which mainly synthesized a (modified) polymer from amylose V. As observed by TLC, MOS of DP 2 to 5 accumulated from the various polymeric substrates, reflecting that *L. fermentum* GTFB requires maltohexaose or longer MOS as glucose donor substrates.

Figure 7:
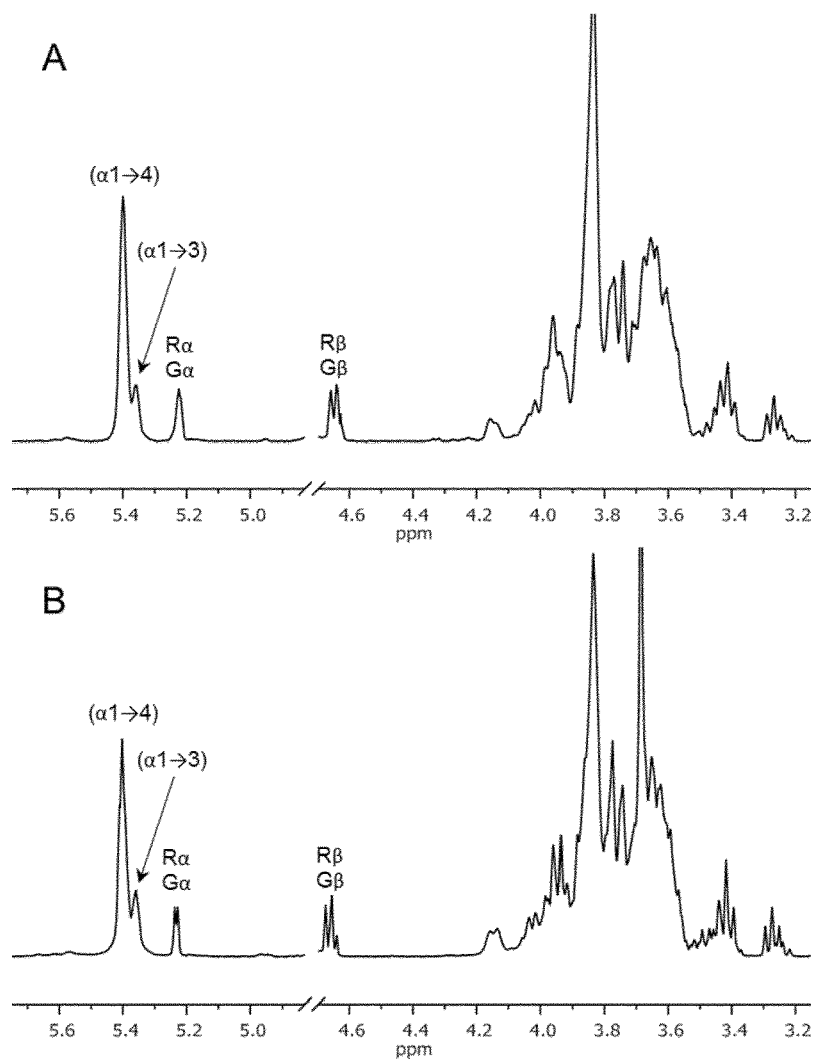
FIG. 7 is $^1$H NMR spectra (D$_2$O, 300K) of the product mixtures formed after incubation of 25 μg ml$^{-1}$ of *L. fermentum* GTFB enzyme with 25 mM maltoheptaose (DP7) (A) and 0.6% (w v$^{-1}$) amylose V (B) for 24 h at 37° C. and pH 5.5. The anomeric signals indicated as Gα/β and Rα/β correspond to free glucose and reducing –(1→4)-D-Glcp units, respectively. Chemical shifts are given in parts per million relative to the signal of internal acetone (δ 2.225).

Aiming to study the product specificity of the *L. fermentum* GTFB, the maltoheptaose and amylose V derived product mixtures were analyzed by one-dimensional $^1$H NMR spectroscopy (FIG. 7). The $^1$H-NMR spectra of both product mixtures revealed the presence of two groups of anomeric overlapping signals at δ ~5.40 and 5.35 corresponding to (α1→4) linkages and newly synthesized (α1→3) linkages. The presence of (α1→3) linkages was corroborated by the structural-reporter-group signal for (α1→3) linkages at δ$_{H-5}$ 4.16 ppm. The spectra also showed signals corresponding to free glucose units (Gα H-1, δ 5.225; Gβ H-1, δ 4.637) and 4-substituted reducing-end glucose residues (Rα H-1, δ 5.225; Rβ H-1, δ 4.652). Small signals corresponding to trace amounts (less than 1%) of (α1→6) linkages (H-1, δ~4.97) were detected. The molar ratios of the (α1→4)-linked, (α1→3)-linked glucose residues for maltoheptaose and amylose V products were 86:14 and 81:19, respectively. Methylation analysis of the product mixture generated by the *L. fermentum* GTFB from amylose V showed the presence of terminal, 3-substituted, 4-substituted, and 3,4-disubstituted glucopyranose residues in a molar percentage of 25, 16, 55, and 4%, which is in agreement with the linkage ratios determined by IId NMR and confirms that the *L. fermentum* GTFB exhibits (α1→3) linkage specificity. In contrast to the *L. reuteri* GTFB enzyme that only generates linear (α1→6) glucan chains (4,6-α-GTase), the *L. fermentum* GTFB acts as a 4,3-α-glucanotransferase (4,3-α-GTase) catalyzing the cleavage of (α1→4) linkages and the formation of new (α1→3) in linear or branched orientations.

Figure 8:
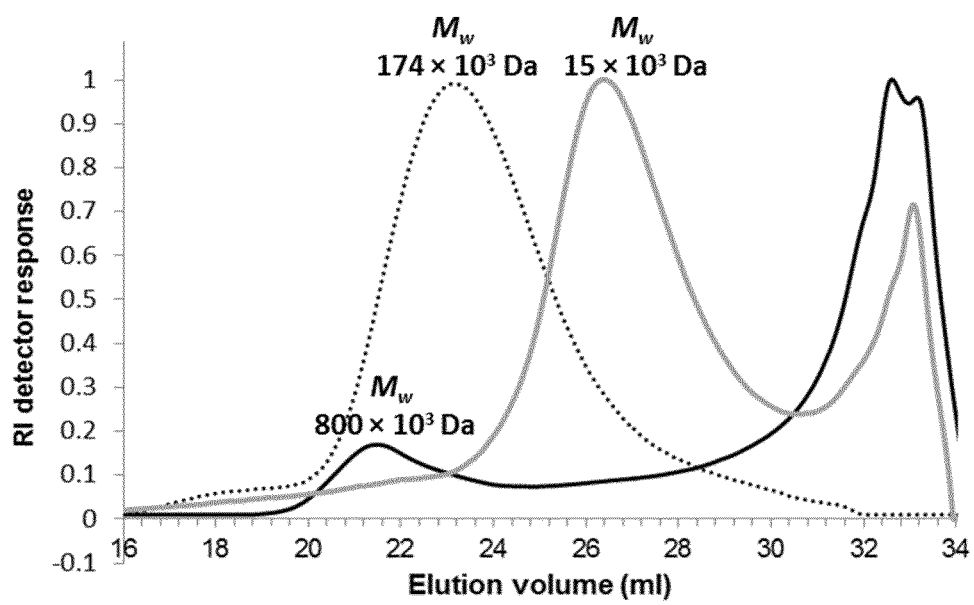
FIG. 8 shows the HPSEC molecular mass distribution of the reaction products generated after the incubation of 0.6% (w v$^{-1}$) amylose V with 25 μg ml$^{-1}$ of *L. fermentum* GTFB (pH 5.5) and *L. reuteri* 121 GTFB (pH 5.0) enzyme for 24 h at 37° C. The dashed line corresponds to the elution profile of the amylose V. The solid black and grey lines correspond to the elution profiles of products synthesized by *L. fermentum* and *L. reuteri* 121 GTFB enzymes, respectively.

The action of the *L. fermentum* GTFB enzyme on amylose was also characterized by HPSEC with multidetection (FIG. 8). The HPSEC profile of the starting amylose V substrate exhibited a single peak eluting at 23.0 ml, with an average M$_w$ of 174×10$^3$ Da, whereas *L. fermentum* GTFB-treated amylose V showed two different molecular mass distribution peaks: An early peak eluting at 21.5 ml corresponding to a high molecular mass polymer with an average M$_w$ of 800× 10$^3$ Da and, a second peak corresponding to oligosaccharides with an average M$_w$ of 1400 Da. In case of the *L. reuteri* 121 GTFB 4,6 α-GT, the peak corresponding to the IMMP eluted at 26.5 ml and had an average M$_w$ of 15×10$^3$ Da. Thus, the L. fermentum GTFB is capable of synthesizing a polymer with a $M_w$ value about 8 and 50 times higher than those of the starting amylose V substrate and the IMMP product, respectively. However, based on the refractive index signal this polymer represents less than 20% of the total product mixture, while a significant proportion of low molecular mass glucans are present in the product mixture of the L. fermentum GTFB.

Structural Characterization of the Products Synthesized by the L. fermentum GTFB from Amylose V For a more detailed structural characterization, the products produced by the L. fermentum GTFB from amylose were purified by size-exclusion chromatography on Biogel P2. The seven fractions obtained, designated as F1-F7, were analyzed separately by MALDI-TOF MS and $^1$H NMR spectroscopy (Table 2). Fractions F6 and F7 contained the hydrolysis products maltotriose (DP3) and maltose (DP2), respectively, and were not further studied. The 1D $^1$H NMR spectrum (FIG. 7) showed α-anomeric signals at δ 5.41 and 5.37; this region may contain anomeric signals of both (α1→4) and (α1→3) linked α-D-Glcp residues. Therefore, fractions F1-F5 were also subjected to methylation analysis in order to determine the presence of (α1→4) and (α1→3) linkages and to determine the degree of branching. The methylation analysis data fit with the peak at δ 5.37 corresponding to (α1→3)-linked residues (Table 2). The $^1$H NMR and methylation analysis of the Biogel P2 fractions demonstrated that the percentage of (α1→3) linkages increased with increasing DP of the products (Table 2). The highest molecular mass product F1 containing polymeric material of DP >30 showed an increased percentage of →3)G1cp (1→glucosyl units (28%) and branching →3,4)G1cp (1→glucosyl units (8%) over those in the total reaction product mixture, 16 and 4%, respectively.

TOCSY spectra with 60 ms (not shown) and 150 ms (FIG. 9) mixing time allowed for elucidation of three H-3 signals at δ 3.70, 3.85 and 3.97, and H-4 signals at δ 3.65-3.67 and 3.42, respectively. In case of a terminal α-D-Glcp-(1→4)-residue H-2, H-3 and H-4 signals are expected at δ 3.57, 3.71 and 3.42, respectively, for a (1→4)-α-D-Glcp-(1→4)-residue H-2, H-3 and H-4 are expected at δ 3.63, 3.96 and 3.65, respectively, whereas a (1→3)-α-D-Glcp-(1→4)-residue should render H-2, H-3 and H-4 at δ 3.68, 3.85 and 3.65, respectively. The 2D $^{13}$C-$^1$H HSQC spectrum showed the $^{13}$C chemical shifts, correlating with the $^1$H chemical shifts expected for these residues. Most notably the 4-substituted C-4 value at δ 78.8, correlated with H-4 at δ 3.65, and C-3 at δ 80.4, correlating with H-3 at δ 3.85 ppm. The data observed in the 2D NMR spectra fit with the occurrence of these three types of residues.

In the δ 5.37 anomeric track the 2D $^1$H-$^1$H COSY spectrum (FIG. 9) showed H2 signals at δ 3.57 and 3.61, indicating the presence of at least two types of residue. The 2D $^1$H-$^1$H TOCSY spectra revealed H-3 signals at δ 3.75 and 4.03, H-4 signals at δ 3.67 and 3.43, and an H-5 signal at δ 4.16, respectively. The signals for H-2-H-4 at δ 3.57, 3.75, 3.43, respectively correspond with those expected for a terminal α-D-Glcp-(1→3)-unit. The H-5 signal for this unit is expected at δ 4.02, which overlaps with the strong H-3 signal at that same chemical shift. The 2D $^{13}$C-$^1$H HSQC spectrum (FIG. 9) shows a C-5 (δ 72.4) and a C-3 value (δ 74.3) correlating with the $^1$H chemical shift at δ 4.02, indicating the occurrence with H-5 at δ 4.02 as expected for the terminal α-D-Glcp-(1→3)-residue. The remaining combination of δ 3.61, 4.03, 3.67 and 4.16 for H-2-H-5 are in line with a -(1→4)-α-D-Glcp-(1→3)-residue. The 2D $^{13}$C-$^1$H HSQC spectrum (FIG. 9) confirms the assignment of the $^1$H chemical shifts, showing unsubstituted C-4 values δ

TABLE 2

Linkage composition of the fractions (F1-F7) yielded by size-exclusion chromatography on Biogel P2 of the product mixture obtained from the incubation of 0.6% (w v$^{-1}$) amylose V with 25 μg ml$^{-1}$ of L. fermentum GTFB.

| | | Chemical shift (%) $^a$ | | Methylation analysis (%) $^b$ | | | |
|---|---|---|---|---|---|---|---|
| Sample | DP | (α1→4) | (α1→3) | Glcp(1→ | 3)-Glcp-(1→ | →4)-Glcp-(1→ | →3,4)-Glcp-(1→ |
| F1 | >30 | 60 | 40 | 6 | 28 | 58 | 8 |
| F2 | ~8-20 | 71 | 29 | 12 | 21 | 61 | 6 |
| F3 | ~6-8 | 80 | 20 | 14 | 15 | 66 | 5 |
| F4 | ~5-6 | 88 | 12 | 21 | 10 | 67 | 2 |
| F5 | ~4-5 | 89 | 11 | 21 | 10 | 64 | 5 |
| F6 | ~3 | 100 | 0 | ND | ND | ND | ND |
| F7 | ~2 | 100 | 0 | ND | ND | ND | ND |

$^a$ The data represent the ratios of integration of the peak areas of the (α1→4) linkage signal at 5.41 ppm and the (α1→3) linkage signal at 5.37 ppm in the $^1$H NMR spectra.
$^b$ The linkage distribution data are shown in molar percentages based on GLC intensities.

Figure 9:
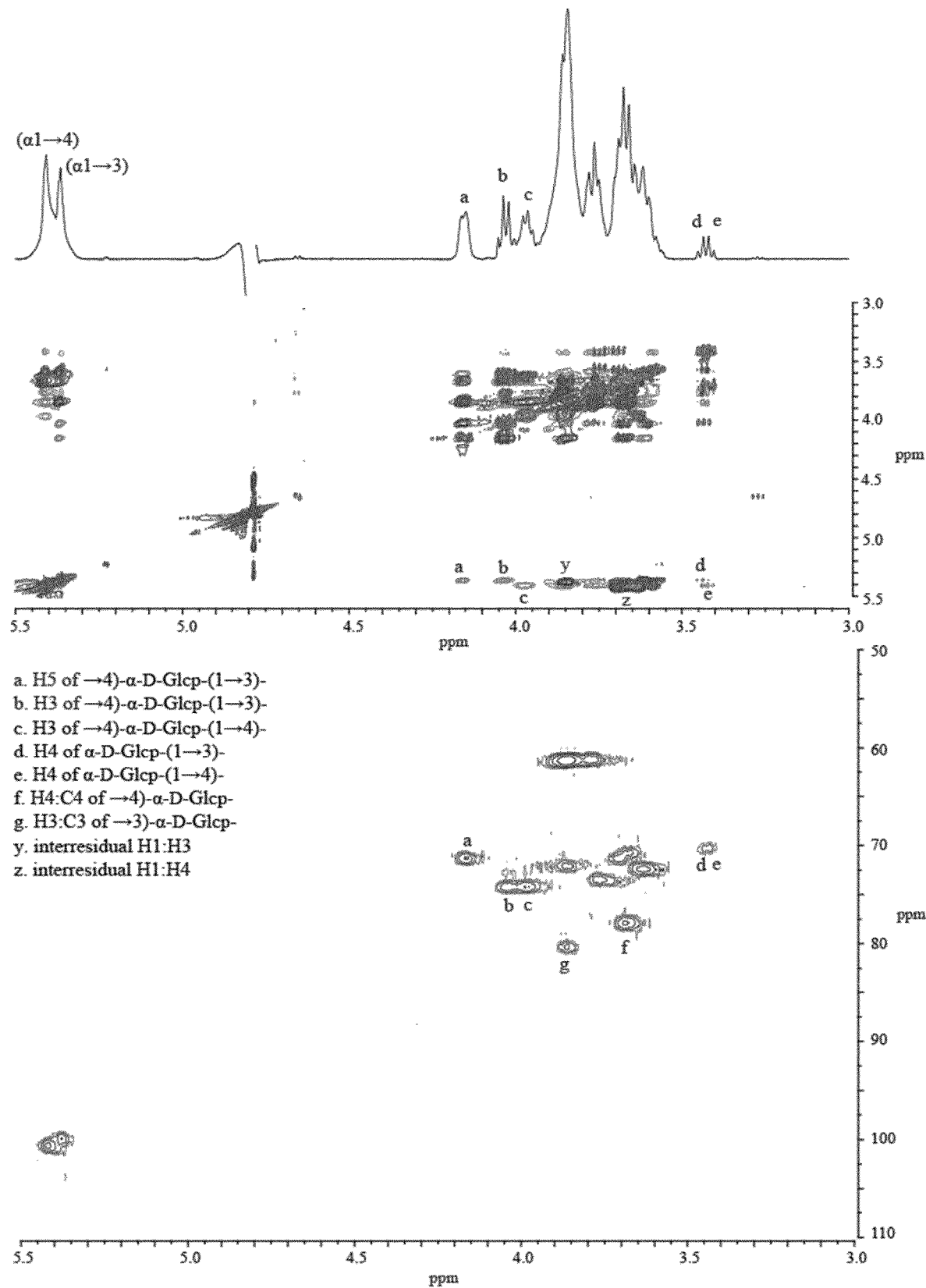
FIG. 9 is a 500-MHz 1D 1HNMR spectrum, 2D $^1$H-$^1$H COSY, TOCSY spectra (mixing time 150 ms), ROESY and 2 D $^{13}$C-$^1$H HSQC spectrum of the Bio-Gel P-2 polysaccharide fraction F1, obtained after 24 h incubation of 0.6%

To unravel the structural elements present in fraction F1, 2D NMR ($^{13}$C-$^1$H HSQC, $^1$H-$^1$H TOCSY, and $^1$H-$^1$H ROESY) experiments were performed (FIG. 9).

Structural Analysis of the Polymeric Fraction F1

The 1D $^1$H NMR spectrum (FIG. 9) of the polysaccharide product (F1) showed sharp anomeric signals at δ 5.41 and δ 5.37 ppm, fitting the presence of (α1→4) and (α1→3) linked glucose units, respectively, in a 6:4 ratio, fitting with the methylation analysis data (Table 2). Table 3 summarizes the NMR data.

In the δ 5.41 anomeric track at least three overlapping types of residues were observed, as evident from the H2 signals in the 2D $^1$H-$^1$H COSY spectrum (FIG. 9) at δ 3.59, 3.63 and 3.69, respectively. Further analysis in the 2D 71.2, correlating with H-4 at δ 3.65, fitting with the 4-substituted α-D-Glcp-(1→3)-residue. Although no distinct signals were found for 3,4-disubstituted residues, there is a significant amount of terminal residues observed as indicated by the structural-reporter signals at δ 3.42 and 3.43 ppm, representing 8.4% in relation to the anomeric signals. Since only (α1→4) and (α1→3) anomeric signals are observed, the branched residues have to be 3,4-disubstituted. This is further supported by the methylation analysis data (Table 2) indicating approximately 8% 3,4-disubstituted residues in F1.

Notably, the (α1→3)-anomeric track showed no H-3 signals at δ 3.85, whereas the 2D $^{13}$C-$^1$H HSQC spectrum showed only 3-substituted C-3 (δ 80.4) correlating with H-3 at δ 3.85, and the 2D $^1$H-$^1$H ROESY spectrum (FIG. 9, red) showed inter-residual correlations between the (α1→3)-anomeric signal only with H-3 at δ 3.85, indicating that no sequential (α→3)-linkages occur. Moreover, the 4-substituted C-4:H-4 signal is only observed at δ 78.8:3.65-3.67 ppm.

TABLE 3

$^1$H and $^{13}$C chemical shifts determined from 1D and 2D NMR spectroscopy for *L. fermentum* GTFB polymer product fraction F1.

| | A | | B | | C | | D | | E | | F | |
|---|---|---|---|---|---|---|---|---|---|---|---|---|
| | $^1$H | $^{13}$C | $^1$H | $^{13}$C | $^1$H | $^{13}$C | $^1$H | $^{13}$C | $^1$H | $^{13}$C | $^1$H | $^{13}$C |
| 1 | 5.41 | 100.6 | 5.41 | 100.6 | 5.37 | 100.0 | 5.41 | 100.6 | 5.41 | 100.6 | 537 | 100.0 |
| 2 | 3.63 | 72.3 | 3.69 | 71.3 | 3.61 | 72.3 | 3.69 | 71.3 | 3.59 | 72.3 | 3.57 | 72.3 |
| 3 | 3.97 | 74.2 | 3.85 | 80.4 | 4.03 | 74.2 | 3.85 | 80.4 | 3.70 | 73.5 | 3.75 | 73.5 |
| 4 | 3.65 | 77.8 | 3.66 | 71.3 | 3.67 | 77.8 | 3.66 | 77.8 | 3.42 | 70.3 | 3.43 | 70.3 |
| 5 | 3.85 | 72.0 | 3.75 | 73.5 | 4.16 | 71.3 | 3.85 | 72.0 | 3.75 | 73.5 | 4.02 | 72.9 |
| 6a | 3.87 | 61.3 | 3.87 | 61.3 | 3.87 | 61.3 | 3.87 | 61.3 | 3.87 | 61.3 | 3.87 | 61.3 |
| 6b | 3.77 | | 3.77 | | 3.77 | | 3.77 | | 3.77 | | 3.77 | |

Smith Degradation Analysis

In order to confirm the absence of consecutive (α→3)-linkages a sample of F1 was subjected to Smith degradation with NaIO$_4$ under mildly acidic conditions, followed by reduction with NaBH$_4$ and mild hydrolysis with formic acid. Considering the linkage analysis, fragments of [α-D-Glcp-(1→3)-]$_n$α-D-Glcp-(142)-L-erythritol are to be expected, and due to over-hydrolysis erythritol and [α-D-Glcp-(1→3)-]$_n$D-Glcp fragments. HPAEC-PAD analysis showed fragment peaks between 2 and 6 min elution time. Since fragments of [α-D-Glcp-(1→3)-]$_n$α-D-Glcp-(1→2)-L-erythritol and [α-D-Glcp-(1→3)-]$_n$D Glcp with n≥1 are expected at retention times above 10 min these results support the suggested absence of consecutive (α1→3)-linkages.

Constructing a Composite Model for F1

The structural reporter signals at δ 3.43 and 3.42, for α-D-Glcp-(1→3)- and α-D-Glcp-(1→4)-residues, respectively in the 1D $^1$H NMR spectrum of F1 indicate 8.4% branching to occur. The relative intensities of the two distinctive peaks are equal, indicating 4.2% α-D-Glcp-(1→3)-residues and 4.2% α-D-Glcp-(1→4)-residues. Taking into account that there are no consecutive (α1→3)-linked residues, all 3-substituted residues must be (α1→4)-linked. Also the branched residues are (1→3,4)-α-D-Glcp-(1→4)-residues, amounting to 8.4%. Since 40% (α1→3) linkages are observed 31.6% of the residues have to be –(1→3)-α-D-Glcp-(1→4)-residues. Since 4.2% of (α1→3)-linked residues are terminal, there are 35.8%–(1→4)-α-D-Glcp-(1→3)-residues. This leaves 15.8%–(1→4)-α-D-Glcp-(1→4)-residues. Taking together all data from 1D and 2D NMR spectroscopy analysis, methylation analysis and Smith Degradation analysis, a composite model for F1 was constructed, showing all identified structural elements in the correct relative abundance (FIG. 10).

Oligosaccharides Formed in Time from Maltoheptaose and Amylose V by the *L. fermentum* GTFB Enzyme To gain a better understanding of the action pattern of the *L. fermentum* GTFB enzyme, time course experiments were performed with the maltoheptaose and amylose V substrates. The oligosaccharide products formed after 10 min, 1 h and 24 h of reaction were analyzed by HPAEC. At the early stage of the reaction with maltoheptaose (slightly contaminated with G6 and G5), G2 was identified as the main reaction product (FIG. 11A). Small peaks corresponding to glucose (G1) and maltotriose (G3) were also identified, whereas a peak with an unknown structure but with a high DP eluted at 58 min. The release of G2, together with the synthesis of a compound with a higher DP, suggests that the *L. fermentum* GTFB enzyme catalyzes the transfer of a maltopentaosyl unit to a MOS acceptor substrate. Later in time, the amounts of glucose and MOS with DP2 to 5 increased, whereas after 24 h G6 and G7 had become depleted. In addition, as a result of the *L. fermentum* GTFB disproportionating activity, peaks that did not fit the MOS retention times and probably corresponding to oligosaccharides containing (1→3) linkages, were detected at shorter and longer retention times than that of the G7 starting substrate. Incubation with the amylose V yielded G2 as the first clear reaction product, together with G1, G3, G4, G5 (FIG. 12A). These profiles significantly differed from the ones obtained with the *L. reuteri* 121 GTFB enzyme when both G7 and amylose V are used as substrates (FIGS. 11B and 12B). With both substrates the *L. reuteri* 121 GTFB releases glucose (instead of G2) as the main first product at the beginning of the reaction. The pronounced accumulation of MOS with DP2 to DP5 by the *L. fermentum* GTFB was not seen for the *L. reuteri* 121 GTFB. These results suggest that the *L. fermentum* and *L. reuteri* 121 GTFB enzymes differ in their mechanism of polymerization. The novel *L. fermentum* GTFB enzyme preferentially catalyzes the transfer of MOS of low DP, showing a mode of action more resembling that of the *A. chroococcum* GTFD enzyme. On the other hand, the *L. fermentum* GTFB 4,3-α-GT seems to require MOS of a certain minimum length (at least DP6) to act on and to produce an α-glucan with an α(1→3)/(1→4) alternating structure and with α(1→3) branching points. Finally, the data indicate that the *L. fermentum* GTFB 4,3-α-GT may present more than one donor binding subsite, as observed in the case of enzymes belonging to the evolutionary related GH13 and GH77 families.

Enzymatic Treatment of the *L. fermentum* GTFB Product

To further characterize the polymer synthesized by the *L. fermentum* GTFB enzyme (Biogel P2 fraction F1), this α-glucan was treated with a high activity dose of α-amylase, dextranase and pullulanase enzymes. The polymer produced by *L. fermentum* GTFB was resistant to the endo-(1→4)-hydrolase activity of α-amylase. As revealed by TLC analysis, only trace amounts of glucose, maltose and high molecular mass oligosaccharides were detected after 48 h of αα-amylase digestion (FIG. 13). Under the same reaction conditions, the starch control substrate was completely hydrolyzed, indicating that the presence of α-(1→3) linkages makes the *L. fermentum* GTFB polymer resistant to α-amylase digestion. The *L. fermentum* GTFB polymer was also subjected to dextranase and pullulanase enzymatic treatments. Dextranase catalyzes the endohydrolysis of consecutive (1→6) linkages in dextran, while pullulanase cleaves the (1→6) linkages present in pullulan, amylopectin and α- and β-limit dextrins of starch. Thus, for the dextranase and the pullulanase treatments, the polymers produced from amylose V by the L. reuteri GTFB and the A. chroococcum GTFD were included as positive controls, respectively. As expected, dextranase efficiently hydrolyzed the IMMP produced by the L. reuteri 121 GTFB, whereas pullulanase completely digested the reuteran-like polymer synthesized by the A. chroococcum GTFD enzyme. In contrast, no hydrolysis was observed in the case of the L. fermentum GTFB polymer, which is in agreement with the absence of (1→6) linkages (less than 1%) deduced from the $^1$H NMR analysis.

CONCLUSIONS

This work has identified and characterized the first GH70 enzyme cleaving (α1→4)-linkages and synthesizing (α1→3)-linkages, encoded by L. fermentum NCC 2970. The inventors propose to name this enzyme (α1→4)-α-D-glucan: (α1→4), (α1→3)-α-D-glucan α-glucanotransferase, in short 4,3-α-glucanotransferase. Regarding its primary sequence, this protein clearly belongs to the novel GTFB-like GH70 subfamily which originally only comprised 4,6-α-glucanotransferases, however, it also possesses unique variations in residues forming the acceptor binding subsites of GSs suggesting that its active site display distinctive features. In accordance with these findings, the L. fermentum GTFB resembles previously characterized GTFB enzymes in using maltodextrins and starch as substrates, but instead of catalyzing the synthesis of consecutive (α1→6) linkages, it displays an (α1→3) linkage specificity. The L. fermentum activity results in the synthesis of an unique α-glucan built up with different lengths of malto-oligosaccharides, interconnected by single (α1→3) linkages in linear and branched orientations.

Even though GSs have a wide product spectrum and synthesize various types of linkages, none of the GSs characterized so far produce an α-glucan consisting of (α1→4)- and (α1→3)-linkages. The structure of the L. fermentum GTFB product also differs from that corresponding to α-glucans containing both (α1→4)- and (α1→3)-linkages found in different lichens and fungi. Indeed, most of these polysaccharides have linear structures, whereas others are mainly composed of (α1→3)-linkages and/or do not present (α1→3,4)-branching points. The direct action of the L. fermentum GTFB on the starch present in food matrices provides starch derivatives which have structural features consistent with low digestibility.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10808271B2). An electronic copy of the "Sequence Listing" will also be available from the USPTO upon request and payment of the fee set forth in 37 CFR 1.19(b)(3).

The invention claimed is:

1. A method of producing an α-glucan containing (α1-3) linked D-glucose units, the method comprising contacting a polysaccharide or oligosaccharide substrate comprising at its non-reducing end at least two (α1-4) linked D-glucose units with an α-glucanotransferase enzyme capable of cleaving (α1-4) glucosidic linkages and making new (α1-3) glucosidic linkages to form a glucose polymer having linear segments of (α1-4) linked D-glucose units interspersed with (α1 >3) glucosidic linkages, without forming consecutive (α1-3) glucosidic linkages, wherein the α-glucanotransferase comprises an amino acid sequence having at least 90% identity to SEQ ID NO:1.

2. The method according to claim 1 wherein the α-glucanotransferase comprises an amino acid sequence having at least 92% identity to SEQ ID NO:1.

3. The method according to claim 1 wherein the α-glucanotransferase is a Lactobacillus fermentum GTFB enzyme.

4. The method according to claim 1 wherein the substrate has a degree of polymerization of at least five.

5. The method according to claim 1 wherein the substrate is selected from the group consisting of starch, starch derivatives, malto-oligosaccharides, gluco-oligosaccharides, amylose, amylopectin, maltodextrins, (α1-4) glucans and combinations thereof.

6. The method according to claim 1 wherein the substrate is comprised within cereal flour.

7. The method according to claim 1 wherein the α-glucanotransferase comprises an amino acid sequence having at least 95% identity to SEQ ID NO:1.

8. The method according to claim 1 wherein the α-glucanotransferase comprises an amino acid sequence having at least 96% identity to SEQ ID NO:1.

9. The method according to claim 1 wherein the α-glucanotransferase comprises an amino acid sequence having at least 97% identity to SEQ ID NO:1.

10. The method according to claim 1 wherein the α-glucanotransferase comprises an amino acid sequence having at least 98% identity to SEQ ID NO:1.

11. The method according to claim 1 wherein the α-glucanotransferase comprises an amino acid sequence having at least 99% identity to SEQ ID NO:1.

* * * * *